(12) United States Patent
Schor et al.

(10) Patent No.: US 7,351,810 B1
(45) Date of Patent: Apr. 1, 2008

(54) POLYPEPTIDES, POLYNUCLEOTIDES AND USES THEREOF

(75) Inventors: Seth Lawrence Schor, Dundee (GB); Ana Maria Schor, Dundee (GB)

(73) Assignee: University of Dundee, Dundee (GB)

( * ) Notice: Subject to any disclaimer, the term of this patent is extended or adjusted under 35 U.S.C. 154(b) by 0 days.

(21) Appl. No.: 09/581,651

(22) PCT Filed: Dec. 15, 1998

(86) PCT No.: PCT/GB98/03766

§ 371 (c)(1),
(2), (4) Date: Oct. 10, 2000

(87) PCT Pub. No.: WO99/31233

PCT Pub. Date: Jun. 24, 1999

(30) Foreign Application Priority Data

Dec. 16, 1997 (GB) .................................. 9726539.1

(51) Int. Cl.
C07H 21/04 (2006.01)
(52) U.S. Cl. ..................... 536/23.1; 536/23.5; 530/350
(58) Field of Classification Search ............... 536/23.5, 536/23.1; 435/320.1, 325, 69.1; 530/300, 530/350; 424/185.1; 514/2
See application file for complete search history.

(56) References Cited

U.S. PATENT DOCUMENTS

| | | | |
|---|---|---|---|
| 4,980,279 A | | 12/1990 | Peters et al. |
| 5,049,658 A | | 9/1991 | Kimizuka et al. |
| 5,124,155 A | | 6/1992 | Reich |
| 5,300,630 A | | 4/1994 | Matsuura et al. |
| 5,571,679 A | | 11/1996 | Sekiguchi et al. |
| 5,629,291 A | | 5/1997 | Ruoslahti et al. |
| 5,830,700 A | * | 11/1998 | Irani .......................... 435/69.7 |

FOREIGN PATENT DOCUMENTS

| | | |
|---|---|---|
| EP | 0 207 751 | 6/1986 |
| EP | 0 344 134 | 5/1989 |
| WO | WO 90/00567 | 1/1990 |
| WO | WO 94/16085 | 7/1994 |
| WO | WO 99/02674 | 1/1999 |
| WO | WO 99/31233 A1 * | 6/1999 |

OTHER PUBLICATIONS

Schor SL, et al. Cancer Res. Dec. 2003; 63 (24): 8827-36.*
Bendig MM. Genet Eng. 1988; (7): 91-127.*
Bristow AF. Trends Biotechnol. Jul. 1993; 11 (7): 301-5.*
Benoliel AM, et al. J Cell Sci. Sep. 1997; 110 (Pt 17): 2089-97.*
Skolnick J, et al. Trends Biotechnol Jan. 2000; 18 (1): 34-9.*
Lazar E, et al. Mol Cell Biol Mar. 1988; 8 (3): 1247-52.*
Burgess WH, et al. J Cell Biol Nov. 1990; 111 (5 Pt 1): 2129-38.*
Gura T. Science. Nov. 7, 1997; 278 (5340): 1041-2.*
Ward AM. Developmental Oncol. 1985; 21: 91-106.*
Houdebine LM. J Biotechnol. May 31, 1994; 34 (3): 269-87.*
Verma IM, et al. Nature. Sep. 18, 1997; 389 (6648): 239-42.*
Patterson AP. Memorandum (Jan. 14, 2003); pp. 3.*
Pandha HS, et al. Cur Opin Invest Drugs. 2000; 1 (1): 122-34.*
Amalfitano A, et al. Cur Gene Ther. 2002; 2: 111-33.*
Schor et al. (Breast Cancer Res. 2001; 3: 373-379).*
Takada et al. (Mol. Endocrinol. 2000; 14 (5): 733-740).*
Guo et al. (Proc. Natl. Acad. Sci. USA. Jun. 22, 2004; 101 (25): 9205-9210).*
GENBANK Accession No. AJ276395 [gi: 12053816].*
UniProtKB Entry No. P02751 (25 pages).*
Kornblihtt, et al., Primary structure of human fibronectin: differential splicing may generate at least 10 polypeptides from a single gene, EMBO Sequence Database Accession No. X0271; 4:1755-1759(1985).
Kornblihtt et al., Primary structure of human fibronectin: differential splicing may generate at least 10 polypeptides from a single gene, EMBO, (USA) vol. 4 pp. 1755-1759 (1985).
Kornblihtt et al., SWISSPROT Sequence Database Accession No. P02751, (1986).
PIRI Sequence database (1985) Accession Ref. FNHU.
Dean et al., Cloning and analysis of the promoter region of the human fibronectin gene; Proc. Nat;. Acad. Sci, USA, vol. 84, pp. 1876-1880, Apr. 1987.
Hynes et al., EMBL Data library PIR2 AccessionNo. S14428, 1989.
Desimone et al., Identification and characterization of alternatively spliced fibronectin mRNAs expressed in early Xenopus embroys, SWISSPROT Database Accession Ref. FINC_XENLA, Dev. Biol. vol. 149 pp. 357-369 (1992).
Schor, Fibroblast subpopulations as accelerators of tumor progression: The role of migration stimulating factor, Epithelial-Mesenchymal Interactions in Cancer, 1995 pp. 273-296, Switzerland.
Schor et al., Migration stimulating factor (MSF): Its structure mode of action and possible function in health and disease; The Society of Experimental Biology 1993, pp. 235-251, UK.
Grey et al., Purification of the migration stimulating factor produced by fetal and brest cancer patients fibroblasts, Proc. Natl. Acad. Sci, USA, vol. 86, pp. 2438-2422, Apr. 1989.
Schor et al., Fetal-like fibroblasts: their production of migration stimulating factor and role in tumor progression, Mammary Tumorigenesis and Malignant Progression, pp. 277-298, 1994.

(Continued)

*Primary Examiner*—Stephen L. Rawlings
(74) *Attorney, Agent, or Firm*—Knobbe, Martens, Olson & Bear LLP

(57) ABSTRACT

A recombinant polynucleotide encoding migrating stimulating factor (MSF) or variants or fragments or derivatives or fusions thereof or fusions of said variants or fragments or derivatives. Reagents are disclosed which can distinguish MSF and fibronectin, and which can distinguish polynucleotides which encode MSF or fibronectin. These reagents are believed to be useful in, for example, diagnosing cancer. MSF or variants or fragments or derivatives or fusions thereof, or fusions of said variants or fusions or derivatives, are useful in modulating cell migration and in wound healing.

3 Claims, 7 Drawing Sheets

OTHER PUBLICATIONS

Irwin et al., Inter-and intra-site hetrogeneity in the expression of fetal-like phenotypic characteristic by gingival fibroblasts: potential significance for wound healing, Journal of Cell Science, vol. 107, p. 1333-1346 (1994) UK.

Schor et al., Phenotypic heterogeneity in breast fibroblasts: Functional anomaly in fibroblasts from histologically normal tissue adjacent to carcinoma, Int. J. Cancer, vol. 59, pp. 25-32 (1994).

Picardo et al., Migration stimulating activity in serum of breast cancer patients, The Lancet, vol. 337, pp. 130-134, Jan. 19, 1991.

Ellis et al., Antogonistic effects of TGF-β1 and MSF on fibroblast migration and hyaluronic acid synthesis, Possible implications for dermal wound healing, Journal of Cell Science, vol. 102, pp. 447-456 (1992) UK.

Picardo et al., Detection of migration stimulating actvity in wound fluid, Experimental and Molecular Pathology vol. 57, pp. 8-21 (1992).

Schor et al., Heterogeneity amoungst fibroblasats in the production of migration stimulating factor (MSF): Implications for cancer pathogenesis, Cell Motility Factors, pp. 127-146, 1992.

Schor et al., Fibroblasts from cancer patients display a mixture of both feotal and adult-like phenotypic characteristics; Journal of Cell Science, vol. 90, pp. 401-407 (1988) UK.

Schor et al., Feotal and cancer patient fibroblasts produce an autocrine migration stimulating factor not made by normal adult cells, Journal of Cell Science, vol. 90, pp. 391-399 (1988) UK.

Schor et al., Characterizationof migration-stimulating factor (MSF): Evidence of it role in cancer pathogenesis, Cancre Investigation vol. 8(6), pp. 665-667, (1990).

Schor et al., Mechanism of action of the migration stimulating factor produced by fetal and cancer patient fibroblasts: Effect on hyaluronic acid synthesis, In Vitro Cellular Development and Biology, vol. 25, No. 8, pp. 737-746, Aug. 1989.

\* cited by examiner

```
   1  CAAACTTGGT GGCAACTTGC CTCCCGGTGC GGGCGTCTCT CCCCCACCGT
  51  CTCAACATGC TTAGGGGTCC GGGGCCCGGG CTGCTGCTGC TGGCCGTCCA
 101  GTGCCTGGGG ACAGCGGTGC CCTCCACGGG AGCCTCGAAG AGCAAGAGGC
 151  AGGCTCAGCA AATGGTTCAG CCCCAGTCCC CGGTGGCTGT CAGTCAAAGC
 201  AAGCCCGGTT GTTATGACAA TGGAAAACAC TATCAGATAA ATCAACAGTG
 251  GGAGCGGACC TACCTAGGCA ATGCGTTGGT TTGTACTTGT TATGGAGGAA
 301  GCCGAGGTTT TAACTGCGAG AGTAAACCTG AAGCTGAAGA GACTTGCTTT
 351  GACAAGTACA CTGGGAACAC TTACCGAGTG GGTGACACTT ATGAGCGTCC
 401  TAAAGACTCC ATGATCTGGG ACTGTACCTG CATCGGGGCT GGGCGAGGGA
 451  GAATAAGCTG TACCATCGCA AACCGCTGCC ATGAAGGGGG TCAGTCCTAC
 501  AAGATTGGTG ACACCTGGAG GAGACCACAT GAGACTGGTG GTTACATGTT
 551  AGAGTGTGTG TGTCTTGGTA ATGGAAAAGG AGAATGGACC TGCAAGCCCA
 601  TAGCTGAGAA GTGTTTTGAT CATGCTGCTG GGACTTCCTA TGTGGTCGGA
 651  GAAACGTGGG AGAAGCCCTA CCAAGGCTGG ATGATGGTAG ATTGTACTTG
 701  CCTGGGAGAA GGCAGCGGAC GCATCACTTG CACTTCTAGA AATAGATGCA
 751  ACGATCAGGA CACAAGGACA TCCTATAGAA TTGGAGACAC CTGGAGCAAG
 801  AAGGATAATC GAGGAAACCT GCTCCAGTGC ATCTGCACAG GCAACGGCCG
 851  AGGAGAGTGG AAGTGTGAGA GGCACACCTC TGTGCAGACC ACATCGAGCG
 901  GATCTGGCCC CTTCACCGAT GTTCGTGCAG CTGTTTACCA ACCGCAGCCT
 951  CACCCCAGC CTCCTCCCTA TGGCCACTGT GTCACAGACA GTGGTGTGGT
1001  CTACTCTGTG GGGATGCAGT GGCTGAAGAC ACAAGGAAAT AAGCAAATGC
1051  TTTGCACGTG CCTGGGCAAC GGAGTCAGCT GCCAAGAGAC AGCTGTAACC
```

*Fig. 1 (part 1)*

1101 CAGACTTACG GTGGCAACTC AAATGGAGAG CCATGTGTCT TACCATTCAC

1151 CTACAACGAC AGGACGGACA GCACAACTTC GAATTATGAG CAGGACCAGA

1201 AATACTCTTT CTGCACAGAC CACACTGTTT TGGTTCAGAC TCGAGGAGGA

1251 AATTCCAATG GTGCCTTGTG CCACTTCCCC TTCCTATACA ACAACCACAA

1301 TTACACTGAT TGCACTTCTG AGGGCAGAAG AGACAACATG AAGTGGTGTG

1351 GGACCACACA GAACTATGAT GCCGACCAGA AGTTTGGGTT CTGCCCCATG

1401 GCTGCCCACG AGGAAATCTG CACAACCAAT GAAGGGGTCA TGTACCGCAT

1451 TGGAGATCAG TGGGATAAGC AGCATGACAT GGGTCACATG ATGAGGTGCA

1501 CGTGTGTTGG GAATGGTCGT GGGGAATGGA CATGCATTGC CTACTCGCAG

1551 CTTCGAGATC AGTGCATTGT TGATGACATC ACTTACAATG TGAACGACAC

1601 ATTCCACAAG CGTCATGAAG AGGGGCACAT GCTGAACTGT ACATGCTTCG

1651 GTCAGGGTCG GGGCAGGTGG AAGTGTGATC CCGTCGACCA ATGCCAGGAT

1701 TCAGAGACTG GGACGTTTTA TCAAATTGGA GATTCATGGG AGAAGTATGT

1751 GCATGGTGTC AGATACCAGT GCTACTGCTA TGGCCGTGGC ATTGGGGAGT

1801 GGCATTGCCA ACCTTTACAG ACCTATCCAA GCTCAAGTGG TCCTGTCGAA

1851 GTATTTATCA CTGAGACTCC GAGTCAGCCC AACTCCCACC CCATCCAGTG

1901 GAATGCACCA CAGCCATCTC ACATTTCCAA GTACATTCTC AGGTGGAGAC

1951 CTGTGAGTAT CCCACCCAGA AACCTTGGAT ACTGAGTCTC CTAATCTTAT

2001 CAATTCTGAT GGTTTCTTTT TTTCCCAGCT TTTGAGCCAA CAACTCTGAT

2051 TAACTATTCC TATAGCATTT ACTATATTTG TTTAGTGAAC AAACAATATG

2101 TGGTCAATTA AATTGACTTG TAGACTGAAA AAAAAAAAA AAAAAA

*Fig. 1 (part 2)*

```
                    10         20        30        40        50        60
pMSF-1α     NLVATCLPVRASLPHRLNMLRGPGPGLLLLAVQCLGTAVPSTGASKSKRQAQQMVQPQSP
            ||||||||||||||||||||||||||||||||||||||||||||||||||||||||||||
fibronectin NLVATCLPVRASLPHRLNMLRGPGPGLLLLAVQCLGTAVPSTGASKSKRQAQQMVQPQSP
                      10        20        30        40

70        80        90       100       110       120
pMSF-1α     VAVSQSKPGCYDNGKHYQINQQWERTYLGNALVCTCYGGSRGFNCESKPEAEETCFDKYT
            |||||||||||||||||||||||||||||||||:||||||||||||||||||||||||||
fibronectin VAVSQSKPGCYDNGKHYQINQQWERTYLGNVLVCTCYGGSRGFNCESKPEAEETCFDKYT
                  50        60        70        80        90       100

130       140       150       160       170       180
pMSF-1α     GNTYRVGDTYERPKDSMIWDCTCIGAGRGRISCTIANRCHEGGQSYKIGDTWRRPHETGG
            ||||||||||||||||||||||||||||||||||||||||||||||||||||||||||||
fibronectin GNTYRVGDTYERPKDSMIWDCTCIGAGRGRISCTIANRCHEGGQSYKIGDTWRRPHETGG
                 110       120       130       140       150       160

190       200       210       220       230       240
pMSF-1α     YMLECVCLGNGKGEWTCKPIAEKCFDHAAGTSYVVGETWEKPYQGWMMVDCTCLGEGSGR
            ||||||||||||||||||||||||||||||||||||||||||||||||||||||||||||
fibronectin YMLECVCLGNGKGEWTCKPIAEKCFDHAAGTSYVVGETWEKPYQGWMMVDCTCLGEGSGR
                 170       180       190       200       210       220

250       260       270       280       290       300
pMSF-1α     ITCTSRNRCNDQDTRTSYRIGDTWSKKDNRGNLLQCICTGNGRGEWKCERHTSVQTTSSG
            ||||||||||||||||||||||||||||||||||||||||||||||||||||||||||||
fibronectin ITCTSRNRCNDQDTRTSYRIGDTWSKKDNRGNLLQCICTGNGRGEWKCERHTSVQTTSSG
                 230       240       250       260       270       280

310       320       330       340       350       360
pMSF-1α     SGPFTDVRAAVYQPQPHPQPPPYGHCVTDSGVVYSVGMQWLKTQGNKQMLCTCLGNGVSC
            ||||||||||||||||||||||||||||||||||||||||||||||||||||||||||||
fibronectin SGPFTDVRAAVYQPQPHPQPPPYGHCVTDSGVVYSVGMQWLKTQGNKQMLCTCLGNGVSC
                 290       300       310       320       330       340

370       380                   390       400
pMSF-1α     QETAVTQTYGGNSNGEPCVLPFTYNDRT--------------DSTTSNYEQDQKYSFCT
            ||||||||||||||||||||||||||||:||           ||||||||||||||||||
fibronectin QETAVTQTYGGNSNGEPCVLPFTYNGRTFYSCTTEGRQDGHLWCSTTSNYEQDQKYSFCT
                 350       360       370       380       390       400

410       420       430       440       450       460
pMSF-1α     DHTVLVQTRGGNSNGALCHFPFLYNNHNYTDCTSEGRRDNMKWCGTTQNYDADQKFGFCP
            ||||||||:|||||||||||||||||||||||||||||||||||||||||||||||||||
fibronectin DHTVLVQTQGGNSNGALCHFPFLYNNHNYTDCTSEGRRDNMKWCGTTQNYDADQKFGFCP
                 410       420       430       440       450       460
```

*Fig. 2 (part 1)*

```
                   470        480        490        500        510        520
pMSF-1α    MAAHEEICTTNEGVMYRIGDQWDKQHDMGHMMRCTCVGNGRGEWTCIAYSQLRDQCIVDD
           ||||||||||||||||||||||||||||||||||||||||||||| ||||||||||||
fibronectin MAAHEEICTTNEGVMYRIGDQWDKQHDMGHMMRCTCVGNGRGEWTCYAYSQLRDQCIVDD
                   470        480        490        500        510        520

530        540        550        560        570        580
pMSF-1α    ITYNVNDTFHKRHEEGHMLNCTCFGQGRGRWKCDPVDQCQDSETGTFYQIGDSWEKYVHG
           ||||||||||||||||||||||||||||||||||||||||||||||||||||||||||
fibronectin ITYNVNDTFHKRHEEGHMLNCTCFGQGRGRWKCDPVDQCQDSETGTFYQIGDSWEKYVHG
                   530        540        550        560        570        580

590        600        610        620        630        640
pMSF-1α    VRYQCYCYGRGIGEWHCQPLQTYPSSSGPVEVFITETPSQPNSHPIQWNAPQPSHISKYI
           ||||||||||||||||||||||||||||||||||||||||||||||||||||||||||
fibronectin VRYQCYCYGRGIGEWHCQPLQTYPSSSGPVEVFITETPSQPNSHPIQWNAPQPSHISKYI
                   590        600        610        620        630        640

650        660        670        680        690        700
pMSF-1α    LRWRPVSIPPRNLGYKVSXSYQFXWFLFPPAFEPTTLINYSYSIYYICLVNKQYVVNXID
           |||||  :   |    →
                                                                 (SEQ IS NO.: 18)

fibronectin LRWRPKNSVGRWKEATIPGHLNSYTIKGLKPGVVYEGQLISIQQYGHQEVTRFDFTTTST
                   650        660        670        680        690        700

(SEQ IS NO.: 17)
```

*Fig. 2 (part 2)*

| | SEQ ID NO: | Sequence Type | Binding Site |
|---|---|---|---|
| NLVATCLPVRASLPHRLN | [SEQ ID NO: 13] | 5' untranslated region | |
| ¹MLRGPGPGLILLAVQCLGTAVPSTGASKSKR | [SEQ ID NO:14] | Signal | |
| ³²QAQQMVQPQSPVAVSQSKPG | [SEQ ID NO: 15] | NH2-terminal segment | |
| ⁵²CYDNGKHYQINQQWERTYLGNALVCTCYGGSRGFNCESKPEAEET | [SEQ ID NO: 16] | I | |
| ⁹⁷CFDKYTGNTYRVGDTYERPKDSMIWDCTCIGAGRGRISCTIANR | [SEQ ID NO: 38] | I | Fibrin |
| ¹⁴¹CHEGGQSYKIGDTWRRPHETGGYMLECVCLGNGKGEWTCKPIAEK | [SEQ ID NO: 39] | I | Heparin |
| ¹⁸⁶CFDHAAGTSYVGETWEKPYQGWMMVDCTCLGEGSGRITGTSRNR | [SEQ ID NO:40] | I | S. aureus |
| ²³²CNDQDTRTSYRIGDTWSKKDNRGNLLQCICTGNGRGEWKCER | [SEQ ID NO:17] | I | |
| ²⁷³HTSVQTTSSGSGPFTDVRAAVYQPHPQPPYGH | [SEQ ID NO:18] | Connecting strand | |
| ³⁰⁵CVTDSGVVYSVGMQWLKTQGNKQMLCTCLGNGVSCQE | [SEQ ID NO: 19] | I | |
| ³⁴⁵TAVTQTYGGNSNGEPCVLPFTYNDRTDSTTSNYEQDQKYSFCTDH | [SEQ ID NO: 20] | II | |
| ³⁹⁰TVLVQTRGGNSNGALCHFPFLYNNHNYTDCTSEGRRDNMKWCGTT QNYDADQKFGFCPMAAHEEI | [SEQ ID NO: 28] | II | Gelatin |
| ⁴⁵⁵CTTNEGVMYRIGDQWDKQHDMGHMMRCTCVGNGRGEWTCIAYSQLRDQ | [SEQ ID NO: 21] | I | |
| ⁵⁰³CIVDDITYNVNDTFHKRHEEGHMLNCTCFGQGRGRWKCDPVDQ | [SEQ ID NO: 22] | I | |
| ⁵⁴⁵CQDSETGTFYQIGDSWEKYVHGVRYQCYCYGRGIGEWHCQPLQTYPSS | [SEQ ID NO: 23] | I | |
| ⁵⁹⁴SGPVEVFITETPSQPNSHPIQWNAPQPSHISKYILRWRP | [SEQ ID NO. 24] | III | |
| ⁶³³VSIPPRNLGY | [SEQ ID NO: 25] | Unique Sequence | |
| *VS*SYQF*WFLFFPAFEPTTLINYSYSIYYICLVNKQYVVN*IDL*TEKKKKKK[SEQ ID NO: 29-33]3' untranslated region | | | |

*Figure 3*

POLYPEPTIDES, POLYNUCLEOTIDES AND USES THEREOF

The present invention relates to polypeptides, polynucleotides and uses thereof and in particular to migration stimulating factor (MSF).

MSF has been described previously in the following papers. Schor et al (1988) *J. Cell Sci.* 90: 391-399 shows that foetal and cancer patient fibroblasts produce an autocrine migration stimulating factor not made by normal adult cells. Schor et al (1988) *J. Cell Sci.* 90: 401-407, shows that fibroblasts from cancer patients display a mixture of both foetal and adult phenotypic characteristics. Schor et al (1989) *In Vitro* 25: 737-746 describes a mechanism of action of the migration stimulating factor (MSF) produced by fetal and cancer patient fibroblasts and its effect on hyaluronic acid synthesis. Grey et al (1989) *Proc. Natl. Acad. Sci. (USA)* 86: 2438-2442 describes the purification of the migration stimulating factor produced by fetal and cancer patient fibroblasts but no amino acid sequence information is given. It is suggested that MSF has a molecular weight of 70 kDa. Schor & Schor (1990) *Cancer Investig.* 8: 665-667 describes the characterisation of migration stimulating activity (MSF) and gives evidence for its role in cancer pathogenesis. Picardo et al (1991) *Lancet* 337: 130-133 describes the presence of migration stimulating activity in the serum of breast cancer patients. Ellis et al (1992) *J. Cell Sci.* 102: 447-456 describes the antagonistic effects of transforming growth factor-β1 and MSF on fibroblast migration and hyaluronic acid synthesis and discusses the possible implications for wound healing. Picardo et al (1992) *Exp. Mol. Path.* 57: 8-21, describes the identification of migration stimulating factor in wound fluid. Irwin et al (1994) *J. Cell Sci.* 107: 1333-1346, describes the inter- and intra-site heterogeneity in the expression of fetal-like phenotypic characteristics by gingival fibroblasts and discusses the potential significance for wound healing. Schor et al (1994) *Int J. Cancer.* 59: 25-32 describes the phenotypic heterogeneity in breast fibroblasts and discusses functional anomaly in fibroblasts from histologically normal tissue adjacent to carcinoma. Schor et al (1991) In: *Cell Motility Factors* (ed. I Goldberg) pp. 127-146, Birkhauser Press, Basel, describes the heterogeneity amongst fibroblasts in the production of migration stimulating factor (MSF) and discusses implications for cancer pathogenesis. Schor et al (1993) In: *Cell behaviour: Adhesion and Motility*. (ed. G. Evans, C. Wigley and R. Warn) Society for Experimental Biology Symposium No. 47, pp. 234-251, describes the potential structural homology of MSF to the gelatin-binding domain of fibronectin its potential mode of action and possible function in health and disease. A small amount of partial amino acid sequence is given, but this sequence is similar to fibronectin and, in fact, is not present in the MSF which has now been cloned and sequenced in the present work (see below). It is suggested that MSF activity isolated from foetal fibroblast conditioned medium consists of three proteins, one with an apparent molecular weight of 119 kDa and a double of 43 and 33 kDa, and, indeed, it was suggested that MSF could be a proteotytic degradation product of fibronectin. Schor (1995) In: *Epithelial Mesenchymal Interactions in Cancer* (eg. I Goldberg and E Rosen). pp. 273-296. Birkhauser Press, Basel, describes fibroblast subpopulations as accelerators of tumor progression and the potential role of migration stimulating factor. MSF is also discussed in Schor et al (1994) In: Mammary Tumorigenesis and Malignant Progression, Kluwer Academic Publishers, Dickson, R. and Lippman, M. (eds).

Thus, MSF is believed to be produced by fibroblasts obtained from a majority of breast cancer patients and is not made by their normal adult counterparts. It is believed that measuring the levels of MSF, for example, in circulating blood or in serum or in urine, may be useful in identifying patients who have or are susceptible to cancer, or that it may be useful in prognosing the outcome of cancer. MSF producing fibroblasts are present in patients with a number of common epithelial tumours, such as carcinoma of the breast, lung and colon, as well as melanoma, and soft tissue sarcoma.

It is believed that it may be particularly useful to measure the levels of MSF in identifying patients who have or are susceptible to breast cancer, or in prognosing the outcome of breast cancer.

In addition, it is believed that MSF may be useful in wound healing since it is present in a majority of wound fluid samples. The directed migration of fibroblasts into the wound site and the transient increase in hyaluronic acid in granulation tissue during the wound healing response are both consistent with the involvement of MSF. (MSF stimulates the synthesis of a high molecular weight species of hyaluronic acid).

MSF is known to be related to fibronectin since certain antibodies raised to MSF also bind to fibronectin.

Fibronectin is a widely distributed glycoprotein present at high concentrations in most extracellular matrices, in plasma (300 μg/ml), and in other body fluids. Fibronectin is a prominent adhesive protein and mediates various aspects of cellular interactions with extracellular matrices including migration. Its principal functions appear to be in cellular migration during development and wound healing, regulation of cell growth and differentiation, and haemostasis/thrombosis.

Further progress in understanding MSF was hindered by the fact that it has not been clear whether MSF is a degradation or breakdown product of fibronectin, and because MSF appears to be structurally related to fibronectin.

We have now discovered that MSF is not a breakdown product of fibronectin but that it appears, quite unexpectedly, to be a "mini" splice variant of fibronectin. The amino acid sequence of MSF, disclosed for the first time herein, reveals unexpected regions of dissimilarity with fibronectin. This has led to previously unavailable methods of measuring, identifying and localising MSF becoming available. The availability of a polynucleotide encoding MSF, disclosed for the first time herein, makes available methods for producing MSF and useful variants thereof, and makes available new methods of specifically identifying, measuring and localising MSF.

A first aspect of the invention provides a recombinant polynucleotide encoding a polypeptide comprising the amino acid sequence (SEQ ID NO: 1)

N L V A T C L P V R A S L P H R L N

M L R G P G P G L L L L A V Q C L G T A V P S T G A S K S K

R Q A Q Q M V Q P Q S P V A V S Q S K P G C Y D N G K H Y Q

-continued

```
INQQWERTYLGNALVCTCYGGSRGFNCESK
PEAEETCFDKYTGNTYRVGDTYERPKDSMI
WDCTCIGAGRGRISCTIANRCHEGGQSYKI
GDTWRRPHETGGYMLECVCLGNGKGEWTCK
PIAEKCFDHAAGTSYVVGETWEKPYQGWMM
VDCTCLGEGSGRITCTSRNRCNDQDTRTSY
RIGDTWSKKDNRGNLLQCICTGNGREWKC
ERHTSVQTTSSGSGPFTDVRAAVYQPQHP
QPPPYGHCVTDSGVVYSVGMQWLKTQGNKQ
MLCTCLGNGVSCQETAVTQTYGGNSNGEPC
VLPFTYNDRTDSTTSNYEQDQKYSFCTDHT
VLVQTRGGNSNGALCHFPFLYNNHNYTDCT
SEGRRDNMKWCGTTQNYDADQKFGFCPMAA
HEEICTTNEGVMYRIGDQWDKQHDMGHMMR
CTCVGNGREWTCIAYSQLRDQCIVDDITY
NVNDTFHKRHEEGHMLNCTCFGQGRGRWKC
DPVDQCQDSETGTFYQIGDSWEKYVHGVRY
QCYCYGRGIGEWHCQPLQTYPSSSGPVEVF
ITETPSQPNSHPIQWNAPQPSHISKYILRW
RPVSIPPRNLGY
``` or variants or fragments or fusions or derivatives thereof, or fusions of said variants or fragments or derivatives.

FIG. 2 shows the amino acid sequence encoded by the cDNA insert in pMSF1I which contains the coding sequence for human migration stimulating factor (MSF). Preferably the amino acid sequence is based on that between the most N-terminal methionine and the most C-terminal stop codon (which are marked X). Thus, it is preferred if the polynucleotide encodes a polypeptide comprising the amino acid sequence shown in FIG. 2 labelled pMSF1I between positions 19 and 660 (SEQ ID NO: 2) (ie. starting MLRGPG . . . as marked and encoding . . . LGY as marked), or variants of fragments or fusions or derivatives thereof or fusions of said variants or fragments.

Throughout the specification where the term MSF is used, and the context does not indicate otherwise, it includes a polypeptide which has an amino acid sequence given in FIG. 2 labelled pMSF1I and, in particular, the amino acid sequence given between positions 19 and 660 (SEQ ID NO: 2).

Amino acid residues are given in standard single letter code or standard three letter code throughout the specification.

It will be appreciated that the recombinant polynucleotides of the invention are not polynucleotides which encode fibronectin or fragments of fibronectin such as the gelatin binding domain. Preferably, the fragments and variants and derivatives are those that include a polynucleotide which encodes a portion or portions of MSF which are portions that distinguish MSF from fibronectin and which are described in more detail below and by reference to FIG. 2.

The polynucleotide may be DNA or RNA but it is preferred if it is DNA. The polynucleotide may or may not contain introns. It is preferred that it does not contain introns and it is particularly preferred if the polynucleotide is a cDNA.

A polynucleotide of the invention is one which comprises the polynucleotide whose sequence is given in FIG. 1. Thus, a polynucleotide of the invention includes the sequence

```
CAAACTTGGT GGCAACTTGC CTCCCGGTGC GGGCGTCTCT CCCCCACCGT  (SEQ ID NO: 3)
CTCAACATGC TTAGGGGTCC GGGGCCCGGG CTGCTGCTGC TGGCCGTCCA
GTGCCTGGGG ACAGCGGTGC CCTCCACGGG AGCCTCGAAG AGCAAGAGGC
AGGCTCAGCA AATGGTTCAG CCCCAGTCCC CGGTGGCTGT CAGTCAAAGC
AAGCCCGGTT GTTATGACAA TGGAAAACAC TATCAGATAA ATCAACAGTG
```

-continued

```
GGAGCGGACC TACCTAGGCA ATGCGTTGGT TTGTACTTGT TATGGAGGAA

GCCGAGGTTT TAACTGCGAG AGTAAACCTG AAGCTGAAGA GACTTGCTTT

GACAAGTACA CTGGGAACAC TTACCGAGTG GGTGACACTT ATGAGCGTCC

TAAAGACTCC ATGATCTGGG ACTGTACCTG CATCGGGGCT GGGCGAGGGA

GAATAAGCTG TACCATCGCA AACCGCTGCC ATGAAGGGGG TCAGTCCTAC

AAGATTGGTG ACACCTGGAG GAGACCACAT GAGACTGGTG GTTACATGTT

AGAGTGTGTG TGTCTTGGTA ATGGAAAAGG AGAATGGACC TGCAAGCCCA

TAGCTGAGAA GTGTTTTGAT CATGCTGCTG GGACTTCCTA TGTGGTCGGA

GAAACGTGGG AGAAGCCCTA CCAAGGCTGG ATGATGGTAG ATTGTACTTG

CCTGGGAGAA GGCAGCGGAC GCATCACTTG CACTTCTAGA AATAGATGCA

ACGATCAGGA CACAAGGACA TCCTATAGAA TTGGAGACAC CTGGAGCAAG

AAGGATAATC GAGGAAACCT GCTCCAGTGC ATCTGCACAG GCAACGGCCG

AGGAGAGTGG AAGTGTGAGA GGCACACCTC TGTGCAGACC ACATCGAGCG

GATCTGGCCC CTTCACCGAT GTTCGTGCAG CTGTTTACCA ACCGCAGCCT

CACCCCCAGC CTCCTCCCTA TGGCCACTGT GTCACAGACA GTGGTGTGGT

CTACTCTGTG GGGATGCAGT GGCTGAAGAC ACAAGGAAAT AAGCAAATGC

TTTGCACGTG CCTGGGCAAC GGAGTCAGCT GCCAAGAGAC AGCTGTAACC

CAGACTTACG GTGGCAACTC AAATGGAGAG CCATGTGTCT TACCATTCAC

CTACAACGAC AGGACGGACA GCACAACTTC GAATTATGAG CAGGACCAGA

AATACTCTTT CTGCACAGAC CACACTGTTT TGGTTCAGAC TCGAGGAGGA

AATTCCAATG GTGCCTTGTG CCACTTCCCC TTCCTATACA ACAACCACAA

TTACACTGAT TGCACTTCTG AGGGCAGAAG AGACAACATG AAGTGGTGTG

GGACCACACA GAACTATGAT GCCGACCAGA AGTTTGGGTT CTGCCCCATG

GCTGCCCACG AGGAAATCTG CACAACCAAT GAAGGGGTCA TGTACCGCAT

TGGAGATCAG TGGGATAAGC AGCATGACAT GGGTCACATG ATGAGGTGCA

CGTGTGTTGG GAATGGTCGT GGGGAATGGA CATGCATTGC CTACTCGCAG

CTTCGAGATC AGTGCATTGT TGATGACATC ACTTACAATG TGAACGACAC

ATTCCACAAG CGTCATGAAG AGGGGCACAT GCTGAACTGT ACATGCTTCG

GTCAGGGTCG GGGCAGGTGG AAGTGTGATC CCGTCGACCA ATGCCAGGAT

TCAGAGACTG GGACGTTTTA TCAAATTGGA GATTCATGGG AGAAGTATGT

GCATGGTGTC AGATACCAGT GCTACTGCTA TGGCCGTGGC ATTGGGGAGT

GGCATTGCCA ACCTTTACAG ACCTATCCAA GCTCAAGTGG TCCTGTCGAA

GTATTTATCA CTGAGACTCC GAGTCAGCCC AACTCCCACC CCATCCAGTG

GAATGCACCA CAGCCATCTC ACATTTCCAA GTACATTCTC AGGTGGAGAC

CTGTGAGTAT CCCACCCAGA AACCTTGGAT ACTGAGTCTC CTAATCTTAT

CAATTCTGAT GGTTTCTTTT TTTCCCAGCT TTTGAGCCAA CAACTCTGAT

TAACTATTCC TATAGCATTT ACTATATTTG TTTAGTGAAC AAACAATATG

TGGTCAATTA AATTGACTTG TAGACTGAAA AAAAAAAAA AAAAAA
```

It is particularly preferred if the polynucleotide of the invention is one which comprises the polynucleotide whose sequence is given between positions 57 and 1982 (SEQ ID NO: 4) in FIG. 1 since this is believed to be the coding sequence for human MSF.

The invention includes a polynucleotide comprising a fragment of the recombinant polynucleotide of the first aspect of the invention. Preferably, the polynucleotide comprises a fragment which is at least 10 nucleotides in length, more preferably at least 14 nucleotides in length and still more preferably at least 18 nucleotides in length. Such polynucleotides are useful as PCR primers.

A "variation" of the polynucleotide includes one which is (i) usable to produce a protein or a fragment thereof which is in turn usable to prepare antibodies which specifically bind to the protein encoded by the said polynucleotide or (ii) an antisense sequence corresponding to the polynucleotide or to a variation of type (i) as just defined. For example, different codons can be substituted which code for the same amino acid(s) as the original codons. Alternatively, the substitute codons may code for a different amino acid that will not affect the activity or immunogenicity of the protein or which may improve or otherwise modulate its activity or immunogenicity. For example, site-directed mutagenesis or other techniques can be employed to create single or multiple mutations, such as replacements, insertions, deletions, and transpositions, as described in Botstein and Shortle, "Strategies and Applications of In Vitro Mutagenesis," *Science,* 229: 193-210 (1985), which is incorporated herein by reference.

Since such modified polynucleotides can be obtained by the application of known techniques to the teachings contained herein, such modified polynucleotides are within the scope of the claimed invention.

Moreover, it will be recognised by those skilled in the art that the polynucleotide sequence (or fragments thereof) of the invention can be used to obtain other polynucleotide sequences that hybridise with it under conditions of high stringency. Such polynucleotides include any genomic DNA. Accordingly, the polynucleotide of the invention includes polynucleotide that shows at least 55 percent, preferably 60 percent, and more preferably at least 70 percent and most preferably at least 90 percent homology with the polynucleotide identified in the method of the invention, provided that such homologous polynucleotide encodes a polypeptide which is usable in at least some of the methods described below or is otherwise useful. It is particularly preferred that in this embodiment, the polynucleotide is one which encodes a polypeptide containing a portion or portions that distinguish MSF from fibronectin.

It is believed that MSF is found in mammals other than human. The present invention therefore includes polynucleotides which encode MSF from other mammalian species including rat, mouse, cow, pig, sheep, rabbit and so on.

Per cent homology can be determined by, for example, the GAP program of the University of Wisconsin Genetic Computer Group.

DNA-DNA, DNA-RNA and RNA-RNA hybridisation may be performed in aqueous solution containing between 0.1×SSC and 6×SSC and at temperatures of between 55° C. and 70° C. It is well known in the art that the higher the temperature or the lower the SSC concentration the more stringent the hybridisation conditions. By "high stringency" we mean 2×SSC and 65° C. 1×SSC is 0.15M NaCl/0.015M sodium citrate. Polynucleotides which hybridise at high stringency are included within the scope of the claimed invention.

"Variations" of the polynucleotide also include polynucleotide in which relatively short stretches (for example 20 to 50 nucleotides) have a high degree of homology (at least 80% and preferably at least 90 or 95%) with equivalent stretches of the polynucleotide of the invention even though the overall homology between the two polynucleotides may be much less. This is because important active or binding sites may be shared even when the general architecture of the protein is different.

By "variants" of the polypeptide we include insertions, deletions and substitutions, either conservative or non-conservative, where such changes do not substantially alter the activity of the said MSF.

Variants and variations of the polynucleotide and polypeptide include natural variants, including allelic variants and naturally-occurring mutant forms.

MSF may be assessed in bioassays based on its stimulation of adult skin fibroblast migration, for example, as is described in Picardo et al (1991) The Lancet 337, 130-133. In this assay, type I collagen is extracted from rat tail tendons in 3% acetic acid, dialyzed for 2 days against distilled water, and used to make 2 ml collagen gels in 35 mm plastic tissue culture dishes. Collagen gels are overlaid with either 1 ml medium (assay control) or 1 ml of the patient serum fraction. Adult fibroblasts ($2\times10^5$) are plated onto the gel in 1 ml growth medium containing 20% aseptic calf serum a confluent monolayer is produced immediately after the cells attached and spread on the cell surface (1-2 h after plating). With the 2 ml volume of the collagen gel, this procedure results in a final concentration of 5% calf serum in all cultures (assay control and test) and 25% patient serum fraction in the test cultures the 1 ml serum fraction used in the assay is diluted about $\frac{1}{3000}$ from the original serum sample. Migration data are expressed as the percentage of fibroblasts within the three-dimensional gel matrix after 4 days of incubation, determined by counting of the number of cells on the gel surface and within the collagen matrix in fifteen randomly selected fields by means of a Leitz 'Labovert' microscope. More than 1000 cells are counted for each determination. Specificity for MSF may be inferred by neutralization of migration stimulating activity by anti-MSF polyclonal antibodies (as herein disclosed). MSF may also be assayed using immunological techniques such as ELISA and the like.

By "conservative substitutions" is intended combinations such as Gly, Ala; Val, Ile, Leu; Asp, Glu; Asn, Gln; Ser, Thr; Lys, Arg; and Phe, Tyr.

Such variants may be made using the methods of protein engineering and site-directed mutagenesis well known in the art.

Preferably, the variant or variation of the polynucleotide encodes a MSF that has at least 30%, preferably at least 50% and more preferably at least 70% of the activity of a natural MSF, under the same assay conditions.

By "fragment of MSF" we include any fragment which retains activity or which is useful in some other way, for example, for use in raising antibodies or in a binding assay, but which is not a fragment of MSF which could also be a fragment of fibronectin.

By "fusion of MSF" we include said MSF fused to any other polypeptide. For example, the said protein kinase may be fused to a polypeptide such as glutathione-S-transferase (GST) or protein A in order to facilitate purification of MSF, or it may be fused to some other polypeptide which imparts some desirable characteristics on the MSF fusion. Fusions to any variant, fragment or derivative of MSF are also included in the scope of the invention.

A further aspect of the invention provides a replicable vector comprising a recombinant polynucleotide encoding MSF, or a variant, fragment, derivative or fusion of MSF or a fusion of said variant, fragment or derivative.

A variety of methods have been developed to operably link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) Science 239, 487-491. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued 3 Apr. 1984 to Rutter et al, 4,530,901 issued 23 Jul. 1985 to Weissman, 4,582,800 issued 15 Apr. 1986 to Crowl, 4,677,063 issued 30 Jun. 1987 to Mark et al, 4,678,751 issued 7 Jul. 1987 to Goeddel, 4,704,362 issued 3 Nov. 1987 to Itakura et al, 4,710,463 issued 1 Dec. 1987 to Murray, 4,757,006 issued 12 Jul. 1988 to Toole, Jr. et al, 4,766,075 issued 23 Aug. 1988 to Goeddel et al and 4,810, 648 issued 7 Mar. 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps).

Other vectors and expression systems are well known in the art for use with a variety of host cells.

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5×PEB using 6250V per cm at 25?FD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

A further aspect of the invention provides a method of making MSF or a variant, derivative, fragment or fusion thereof or a fusion of a variant, fragment or derivative, the method comprising culturing a host cell comprising a recombinant polynucleotide or a replicable vector which encodes said MSF or variant or fragment or derivative or fusion, and isolating said MSF or a variant, derivative, fragment or fusion thereof of a fusion or a variant, fragment or derivative from said host cell.

Methods of cultivating host cells and isolating recombinant proteins are well known in the art. It will be appreciated that, depending on the host cell, the MSF produced may differ from that which can be isolated from nature. For example, certain host cells, such as yeast or bacterial cells, either do not have, or have different, post-translational modification systems which may result in the production of forms of MSF which may be post-translationally modified in a different why to MSF isolated from nature. It is preferred if the host cell is a non-human host cell; move preferably it is not a mammalian cell.

It is preferred that recombinant MSF is produced in a eukaryotic system, such as an insect cell.

A further aspect of the invention provides MSF or a variant, fragment, derivative or fusion thereof or a fusion of a variant, fragment or derivative obtainable by the methods herein disclosed.

A further aspect of the invention provides a polypeptide comprising the amino acid sequence (SEQ ID NO: 1)

N L V A T C L P V R A S L P H R L N

M L R G P G P G L L L L A V Q C L G T A V P S T G A S K S K

R Q A Q Q M V Q P Q S P V A V S Q S K P G C Y D N G K H Y Q

I N Q Q W E R T Y L G N A L V C T C Y G G S R G F N C E S K

P E A E E T C F D K Y T G N T Y R V G D T Y E R P K D S M I

-continued

```
W D C T C I G A G R G R I S C T I A N R C H E G G Q S Y K I
G D T W R R P H E T G G Y M L E C V C L G N G K G E W T C K
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N G R E W K C
E R H T S V Q T T S S G S G P F T D V R A A V Y Q P Q H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
C T C V G N G R G E W T C I A Y S Q L R D Q C I V D D I T Y
N V N D T F H K R H E E G H M L N C T C F G Q G R G R W K C
D P V D Q C Q D S E T G T F Y Q I G D S W E K Y V H G V R Y
Q C Y C Y G R G I G E W H C Q P L Q T Y P S S S G P V E V F
I T E T P S Q P N S H P I Q W N A P Q P S H I S K Y I L R W
R P V S I P P R N L G Y
``` or variants or fragments or fusions or derivatives thereof or fusions of said variants or fragments or derivatives.

Thus, a polypeptide of the invention includes (SEQ ID NO: 1)
```
N L V A T C L P V R A S L P H R L N
M L R G P G P G L L L L A V Q C L G T A V P S T G A S K S K
R Q A Q Q M V Q P Q S P V A V S Q S K P G C Y D N G K H Y Q
I N Q Q W E R T Y L G N A L V C T C Y G G S R G F N C E S K
P E A E E T C F D K Y T G N T Y R V G D T Y E R P K D S M I
W D C T C I G A G R G R I S C T I A N R C H E G G Q S Y K I
G D T W R R P H E T G G Y M L E C V C L G N G K G E W T C K
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N G R E W K C
E R H T S V Q T T S S G S G P F T D V R A A V Y Q P Q H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
```

-continued

```
C T C V G N G R G E W T C I A Y S Q L R D Q C I V D D I T Y

N V N D T F H K R H E E G H M L N C T C F G Q G R G R W K C

D P V D Q C Q D S E T G T F Y Q I G D S W E K Y V H G V R Y

Q C Y C Y G R G I G E W H C Q P L Q T Y P S S S G P V E V F

I T E T P S Q P N S H P I Q W N A P Q P S H I S K Y I L R W

R P V S I P P R N L G Y
```

Preferably, the polypeptide comprises the amino acid sequence shown in FIG. 2 labelled pMSF1I between positions 19 and 660 (SEQ ID NO: 2), or variants or fragments or fusions or derivatives thereof or fusions of said variants or fragments or derivatives.

It will be appreciated that the polypeptides of the invention are not fibronectin or fragments of fibronectin such as the gelatin binding domain.

Preferably, the fragments and variants and derivatives are those that include a portion or portions of MSF which are portions that distinguish MSF from fibronectin and which are described in more detail below and by reference to FIG. 2.

Preferably, the polypeptide of the invention is one which has migration stimulating factor activity.

Further aspects of the invention provide antibodies which are selective for MSF (and do not cross react with fibronectin) and antibodies which are selective for fibronectin (and do not cross react with MSF).

By "selective" we include antibodies which bind at least 10-fold more strongly to one polypeptide than to the other (ie MSF vs fibronectin); preferably at least 50-fold more strongly and more preferably at least 100-fold more strongly.

Such antibodies may be made by methods well known in the art using the information concerning the differences in amino acid sequence between MSF and fibronectin disclosed herein. In particular, the antibodies may be polyclonal or monoclonal.

Suitable monoclonal antibodies which are reactive as said may be prepared by known techniques, for example those disclosed in "*Monoclonal Antibodies: A manual of techniques*", H Zola (CRC Press, 1988) and in "Monoclonal Hybridoma Antibodies: Techniques and Applications", SGR Hurrell (CRC Press, 1982). Polyclonal antibodies may be produced which are polyspecific or monospecific. It is preferred that they are monospecific.

One embodiment provides an antibody reactive towards the polypeptide whose amino acid sequence is (SEQ ID NO:1)
```
N L V A T C L P V R A S L P H R L N

M L R G P G P G L L L L A V Q C L G T A V P S T G A S K S K

R Q A Q Q M V Q P Q S P V A V S Q S K P G C Y D N G K H Y Q

I N Q Q W E R T Y L G N A L V C T C Y G G S R G F N C E S K

P E A E E T C F D K Y T G N T Y R V G D T Y E R P K D S M I

W D C T C I G A G R G R I S C T I A N R C H E G G Q S Y K I

G D T W R R P H E T G G Y M L E C V C L G N G K G E W T C K

P I A E K C F D H A A G T S Y V V G E T W E K P Y Q G W M M

V D C T C L G E G S G R I T C T S R N R C N D Q D T R T S Y

R I G D T W S K K D N R G N L L Q C I C T G N G R G E W K C

E R H T S V Q T T S S G S G P F T D V R A A V Y Q P Q P H P

Q P P P Y G H C V T D S G V V Y S V G M Q W L K T Q G N K Q

M L C T C L G N G V S C Q E T A V T Q T Y G G N S N G E P C

V L P F T Y N D R T D S T T S N Y E Q D Q K Y S F C T D H T

V L V Q T R G G N S N G A L C H F P F L Y N N H N Y T D C T

S E G R R D N M K W C G T T Q N Y D A D Q K F G F C P M A A

H E E I C T T N E G V M Y R I G D Q W D K Q H D M G H M M R

C T C V G N G R G E W T C I A Y S Q L R D Q C I V D D I T Y

N V N D T F H K R H E E G H M L N C T C F G Q G R G R W K C

D P V D Q C Q D S E T G T F Y Q I G D S W E K Y V H G V R Y
```

-continued

```
Q C Y C Y G R G I G E W H C Q P L Q T Y P S S S G P V E V F
I T E T P S Q P N S H P I Q W N A P Q P S H I S K Y I L R W
R P V S I P P R N L G Y
``` or natural variants thereof but not reactive towards fibronectin.

A further embodiment provides an antibody reactive towards the polypeptide whose amino acid sequence is shown in FIG. 2 labelled pMSF1I between positions 19 and 660 (SEQ ID NO: 2) or natural variants thereof but not reactive towards fibronectin.

A further embodiment provides an antibody reactive towards an epitope present in the polypeptide whose amino acid sequence is shown in FIG. 2 labelled pMSF1I or natural variants thereof but which epitope is not present in fibronectin.

A further embodiment provides an antibody reactive towards an epitope present in the polypeptide whose amino acid sequence is between positions 19 and 660 or natural variants thereof but which is epitope is not present in fibronectin.

It is particularly preferred if the antibody is reactive towards a molecule comprising any one of the peptides:

| | |
|---|---|
| ISKYILRWRP<u>VSIPPRNLGY</u>; or | (SEQ ID NO: 5) |
| QQWERTYLGN<u>A</u>LVCTCYGGSR; or | (SEQ ID NO: 6) |
| PCVLPFTYN<u>DRTD</u>STTSNYEQDQ; or | (SEQ ID NO: 7) |
| TDHTVLVQT<u>R</u>GGNSNGALCH; or | (SEQ ID NO: 8) |
| VGNGRGEWTC<u>I</u>AYSQLRDQCI | (SEQ ID NO: 9) |

(SEQ ID NO:1)
```
N L V A T C L P V R A S L P H R L N
M L R G P G P G L L L L A V Q C L G T A V P S T G A S K S K
R Q A Q Q M V Q P Q S P V A V S Q S K P G C Y D N G K H Y Q
I N Q Q W E R T Y L G N A L V C T C Y G G S R G F N C E S K
P E A E E T C F D K Y T G N T Y R V G D T Y E R P K D S M I
W D C T C I G A G R G R I S C T I A N R C H E G G Q S Y K I
G D T W R R P H E T G G Y M L E C V C L G N G K G E W T C K
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N G R G E W K C
E R H T S V Q T T S S G S G P F T D V R A A V Y Q P Q P H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
C T C V G N G R G E W T C I A Y S Q L R D Q C I V D D I T Y
N V N D T F H K R H E E G H M L N C T C F G Q G R G R W K C
D P V D Q C Q D S E T G T F Y Q I G D S W E K Y V H G V R Y
Q C Y C Y G R G I G E W H C Q P L Q T Y P S S S G P V E V F
I T E T P S Q P N S H P I Q W N A P Q P S H I S K Y I L R W
R P V S I P P R N L G Y
``` which are found in MSF. The underlined amino acid(s) indicate the difference between MSF and fibronectin.

These peptides contain and flank regions of difference in amino acid sequence between MSF and fibronectin as shown in FIG. 2 which are believed to be useful in distinguishing MSF and fibronectin using antibodies.

A further embodiment provides an antibody reactive towards fibronectin but not reactive towards the polypeptide whose amino acid sequence is shown in FIG. 2 labelled pMSF1 or natural variants thereof.

A further embodiment provides an antibody reactive towards fibronectin but not reactive towards the polypeptide whose amino acid sequence is shown in FIG. 2 labelled pMSF1 between positions 19 and 660 (SEQ ID NO: 2) or natural variants thereof.

A further embodiment provides an antibody reactive towards an epitope present in fibronectin but not present in the polypeptide whose amino acid sequence is It is particularly preferred if the antibody is reactive towards a molecule comprising any one of the peptides:

```
QQWERTYLGNVLVCTCYGGSR              (SEQ ID NO: 10)
or (SEQ ID NO: 11)
EPCVLPFTYNGRTFYSCTTEGRODGHLWCSTTSNYEQDQ
or

CTDHTVLVQTQGGNSNGALCH              (SEQ ID NO: 12)
or

VGNGRGEWTCYAYSQLRDQCI              (SEQ ID NO: 13)
or

ISKYILRWRPKNSVGRWKEA               (SEQ ID NO: 14)
```

```
                                                    (SEQ ID NO:1)
N L V A T C L P V R A S L P H R L N

M L R G P G P G L L L L A V Q C L G T A V P S T G A S K S K

R Q A Q Q M V Q P Q S P V A V S Q S K P G C Y D N G K H Y Q

I N Q Q W E R T Y L G N A L V C T C Y G G S R G F N C E S K

P E A E E T C F D K Y T G N T Y R V G D T Y E R P K D S M I

W D C T C I G A G R G R I S C T I A N R C H E G G Q S Y K I

G D T W R R P H E T G G Y M L E C V C L G N G K G E W T C K

P I A E K C F D H A A G T S Y V V G E T W E K P Y Q G W M M

V D C T C L G E G S G R I T C T S R N R C N D Q D T R T S Y

R I G D T W S K K D N R G N L L Q C I C T G N G R G E W K C

E R H T S V Q T T S S G S G P F T D V R A A V Y Q P Q P H P

Q P P P Y G H C V T D S G V V Y S V G M Q W L K T Q G N K Q

M L C T C L G N G V S C Q E T A V T Q T Y G G N S N G E P C

V L P F T Y N D R T D S T T S N Y E Q D Q K Y S F C T D H T

V L V Q T R G G N S N G A L C H F P F L Y N N H N Y T D C T

S E G R R D N M K W C G T T Q N Y D A D Q K F G F C P M A A

H E E I C T T N E G V M Y R I G D Q W D K Q H D M G H M M R

C T C V G N G R G E W T C I A Y S Q L R D Q C I V D D I T Y

N V N D T F H K R H E E G H M L N C T C F G Q G R G R W K C

D P V D Q C Q D S E T G T F Y Q I G D S W E K Y V H G V R Y

Q C Y C Y G R G I G E W H C Q P L Q T Y P S S S G P V E V F

I T E T P S Q P N S H P I Q W N A P Q P S H I S K Y I L R W

R P V S I P P R N L G Y
``` or natural variants thereof.

A further embodiment provides an antibody reactive towards an epitope present in fibronectin but not present in the polypeptide whose amino acid sequence is shown in FIG. 2 labelled pMSF1I between positions 19 and 660 (SEQ ID NO: 2) or natural variants thereof.

peptides derived from position 648 onwards in fibronectin (SEQ ID NO: 15) as shown in FIG. 2. The underlined amino acid(s) indicate the difference between fibronectin and MSF.

These peptides themselves may be useful for raising antibodies, but selective antibodies may be made using smaller fragments of these peptides which contain the region of difference between MSF and fibronectin.

Peptides in which one or more of the amino acid residues are chemically modified, before or after the peptide is synthesised, may be used providing that the function of the peptide, namely the production of specific antibodies in vivo, remains substantially unchanged. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism. The peptides may be present as single copies or as multiples, for example tandem repeats. Such tandem or multiple repeats may be sufficiently antigenic themselves to obviate the use of a carrier. It may be advantageous for the peptide to be formed as a loop, with the N-terminal and C-terminal ends joined together, or to add one or more Cys residues to an end to increase antigenicity and/or to allow disulphide bonds to be formed. If the peptide is covalently linked to a carrier, preferably a polypeptide, then the arrangement is preferably such that the peptide of the invention forms a loop.

According to current immunological theories, a carrier function should be present in any immunogenic formulation in order to stimulate, or enhance stimulation of, the immune system. It is thought that the best carriers embody (or, together with the antigen, create) a T-cell epitope. The peptides may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys (SEQ ID NO: 16), beta-galactosidase and the 163-171 peptide of interleukin-1. The latter compound may variously be regarded as a carrier or as an adjuvant or as both. Alternatively, several copies of the same or different peptides of the invention may be cross-linked to one another; in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4-(N-maleimidomethyl)cyclohexane-1-carboxylate, the latter agent exploiting the —SH group on the C-terminal cysteine residue (if present).

If the peptide is prepared by expression of a suitable nucleotide sequence in a suitable host, then it may be advantageous to express the peptide as a fusion product with a peptide sequence which acts as a carrier. Kabigen's "Ecosec" system is an example of such an arrangement.

The peptide of the invention may be linked to other antigens to provide a dual effect.

A further aspect of the invention provides a method of making an antibody which is reactive towards the polypeptide whose amino acid sequence is (SEQ ID NO:1)
```
N L V A T C L P V R A S L P H R L N
M L R G P G P G L L L L A V Q C L G T A V P S T G A S K S K
R Q A Q Q M V Q P Q S P V A V S Q S K P G C Y D N G K H Y Q
I N Q Q W E R T Y L G N A L V C T C Y G G S R G F N C E S K
P E A E E T C F D K Y T G N T Y R V G D T Y E R P K D S M I
W D C T C I G A G R G R I S C T I A N R C H E G G Q S Y K I
G D T W R R P H E T G G Y M L E C V C L G N G K G E W T C K
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N G R G E W K C
E R H T S V Q T T S S G S G P F T D V R A A V Y Q P Q P H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
C T C V G N G R G E W T C I A Y S Q L R D Q C I V D D I T Y
N V N D T F H K R H E E G H M L N C T C F G Q G R G R W K C
D P V D Q C Q D S E T G T F Y Q I G D S W E K Y V H G V R Y
Q C Y C Y G R G I G E W H C Q P L Q T Y P S S S G P V E V F
```

-continued
```
I T E T P S Q P N S H P I Q W N A P Q P S H I S K Y I L R W

R P V S I P P R N L G Y
``` or a natural variant thereof and which is not reactive with fibronectin, the method comprising the steps of, where appropriate, immunising an animal with a peptide which distinguishes MSF from fibronectin and selecting an antibody which binds MSF but does not substantially bind fibronectin. Suitable peptides are disclosed above.

A still further aspect of the invention provides a method of making an antibody which is reactive towards fibronectin and which is not reactive towards the polypeptide whose amino acid sequence is Before the present invention it was not possible to make use of the differences in amino acid sequence between fibronectin and MSF in order to make antibodies which are useful in distinguishing MSF and fibronectin since it was not known that MSF and fibronectin had significant differences in structure or what those differences were. As is discussed in more detail below, such antibodies are useful in cancer diagnosis. It will also be appreciated that such antibodies which distinguish MSF and fibronectin are also useful research reagents. Suitably, the antibodies of the invention

```
                                                                (SEQ ID NO:1)
N L V A T C L P V R A S L P H R L N

M L R G P G P G L L L L A V Q C L G T A V P S T G A S K S K

R Q A Q Q M V Q P Q S P V A V S Q S K P G C Y D N G K H Y Q

I N Q Q W E R T Y L G N A L V C T C Y G G S R G F N C E S K

P E A E E T C F D K Y T G N T Y R V G D T Y E R P K D S M I

W D C T C I G A G R G R I S C T I A N R C H E G G Q S Y K I

G D T W R R P H E T G G Y M L E C V C L G N G K G E W T C K

P I A E K C F D H A A G T S Y V V G E T W E K P Y Q G W M M

V D C T C L G E G S G R I T C T S R N R C N D Q D T R T S Y

R I G D T W S K K D N R G N L L Q C I C T G N G R G E W K C

E R H T S V Q T T S S G S G P F T D V R A A V Y Q P Q H P

Q P P P Y G H C V T D S G V V Y S V G M Q W L K T Q G N K Q

M L C T C L G N G V S C Q E T A V T Q T Y G G N S N G E P C

V L P F T Y N D R T D S T T S N Y E Q D Q K Y S F C T D H T

V L V Q T R G G N S N G A L C H F P F L Y N N H N Y T D C T

S E G R R D N M K W C G T T Q N Y D A D Q K F G F C P M A A

H E E I C T T N E G V M Y R I G D Q W D K Q H D M G H M M R

C T C V G N G R G E W T C I A Y S Q L R D Q C I V D D I T Y

N V N D T F H K R H E E G H M L N C T C F G Q G R G R W K C

D P V D Q C Q D S E T G T F Y Q I G D S W E K Y V H G V R Y

Q C Y C Y G R G I G E W H C Q P L Q T Y P S S S G P V E V F

I T E T P S Q P N S H P I Q W N A P Q P S H I S K Y I L R W

R P V S I P P R N L G Y
``` or a natural variant thereof, the method comprising the steps of, where appropriate, immunising an animal with a peptide which distinguishes fibronectin from MSF and selecting an antibody which binds fibronectin but does not substantially bind MSF. Suitable peptides are disclosed above.

It will be appreciated that, with the advancements in antibody technology, it may not be necessary to immunise an animal in order to produce an antibody. Synthetic systems, such as phage display libraries, may be used. The use of such systems is included in the methods of the invention.

are detectably labelled, for example they may be labelled in such a way that they may be directly or indirectly detected. Conveniently, the antibodies are labelled with a radioactive moiety or a coloured moiety or a fluorescent moiety, or they may be linked to an enzyme. Typically, the enzyme is one which can convert a non-coloured (or non-fluorescent) substrate to a coloured (or fluorescent) product. The antibody may be labelled by biotin (or streptavidin) and then detected indirectly using streptavidin (or biotin) which has been labelled with a radioactive moiety or a coloured moiety or a fluorescent moiety, or the like or they may be linked to an enzyme of the type described above.

It is particularly preferred if peptides are made, based on the amino acid sequence of MSF and fibronectin, which allow for specific antibodies to be made.

Thus, a further aspect of the invention provides a molecule which is capable of, following immunisation of an animal if appropriate, giving rise to antibodies which are reactive towards the polypeptide whose sequence is or natural variants thereof but not reactive towards fibronectin.

A still further aspect of the invention provides a molecule which is capable of, following immunisation of an animal if appropriate, giving rise to antibodies which are reactive towards fibronectin but not reactive towards the polypeptide whose sequence is (SEQ ID NO:1)
```
N L V A T C L P V R A S L P H R L N
M L R G P G P G L L L L A V Q C L G T A V P S T G A S K S K
R Q A Q Q M V Q P Q S P V A V S Q S K P G C Y D N G K H Y Q
I N Q Q W E R T Y L G N A L V C T C Y G G S R G F N C E S K
P E A E E T C F D K Y T G N T Y R V G D T Y E R P K D S M I
W D C T C I G A G R G R I S C T I A N R C H E G G Q S Y K I
G D T W R R P H E T G G Y M L E C V C L G N G K G E W T C K
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N R G E W K C
E R H T S V Q T T S S G S G P F T D V R A A V Y Q P Q P H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
C T C V G N G R G E W T C I A Y S Q L R D Q C I V D D I T Y
N V N D T F H K R H E E G H M L N C T C F G Q G R G R W K C
D P V D Q C Q D S E T G T F Y Q I G D S W E K Y V H G V R Y
Q C Y C Y G R G I G E W H C Q P L Q T Y P S S S G P V E V F
I T E T P S Q P N S H P I Q W N A P Q P S H I S K Y I L R W
R P V S I P P R N L G Y
```

50

-

(SEQ ID NO:1)
```
N L V A T C L P V R A S L P H R L N
M L R G P G P G L L L L A V Q C L G T A V P S T G A S K S K
R Q A Q Q M V Q P Q S P V A V S Q S K P G C Y D N G K H Y Q
I N Q Q W E R T Y L G N A L V C T C Y G G S R G F N C E S K
P E A E E T C F D K Y T G N T Y R V G D T Y E R P K D S M I
W D C T C I G A G R G R I S C T I A N R C H E G G Q S Y K I
G D T W R R P H E T G G Y M L E C V C L G N G K G E W T C K
```

-continued

```
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N G R G E W K C
E R H T S V Q T T S S G S G P F T D V R A A V Y Q P Q H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
C T C V G N G R G E W T C I A Y S Q L R D Q C I V D D I T Y
N V N D T F H K R H E E G H M L N C T C F G Q G R G R W K C
D P V D Q C Q D S E T G T F Y Q I G D S W E K Y V H G V R Y
Q C Y C Y G R G I G E W H C Q P L Q T Y P S S S G P V E V F
I T E T P S Q P N S H P I Q W N A P Q P S H I S K Y I L R W
R P V S I P P R N L G Y
``` or natural variants thereof.

The molecule is preferably a peptide but may be any molecule which gives rise to the desired antibodies. The molecule, preferably a peptide, is conveniently formulated into an immunological composition using methods well known in the art.

The peptides disclosed above form part of these aspects of the invention.

Peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

It is now possible to make polynucleotides which can distinguish MSF and fibronectin and such polynucleotides are believed to be useful in the diagnosis and prognosis of cancer.

A further aspect of the invention provides a polynucleotide which is capable of distinguishing a polynucleotide which encodes the polypeptide whose sequence is (SEQ ID NO:1)

NLVATCLPVRASLPHRLN
MLRGPGPGLLLLAVQCLGTAVPSTGASKSK
RQAQQMVQPQSPVAVSQSKPGCYDNGKHYQ
INQQWERTYLGNALVCTCYGGSRGFNCESK
PEAEETCFDKYTGNTYRVGDTYERPKDSMI
WDCTCIGAGRGRISCTIANRCHEGGQSYKI
GDTWRRPHETGGYMLECVCLGNGKGEWTCK
PIAEKCFDHAAGTSYVVGETWEKPYQGWMM
VDCTCLGEGSGRITCTSRNRCNDQDTRTSY
RIGDTWSKKDNRGNLLQCICTGNGRGEWKC
ERHTSVQTTSSGSGPFTDVRAAVYQPQPHP
QPPPYGHCVTDSGVVYSVGMQWLKTQGNKQ
MLCTCLGNGVSCQETAVTQTYGGNSNGEPC
VLPFTYNDRTDSTTSNYEQDQKYSFCTDHT
VLVQTRGGNSNGALCHFPFLYNNHNYTDCT
SEGRRDNMKWCGTTQNYDADQKFGFCPMAA
HEEICTTNEGVMYRIGDQWDKQHDMGHMMR
CTCVGNGRGEWTCIAYSQLRDQCIVDDITY
NVNDTFHKRHEEGHMLNCTCFGQGRGRWKC
DPVDQCQDSETGTFYQIGDSWEKYVHGVRY
QCYCYGRGIGEWHCQPLQTYPSSSGPVEVF
ITETPSQPNSHPIQWNAPQPSHISKYILRW
RPVSIPPRNLGY or a natural variant thereof and a polynucleotide which encodes fibronectin.

A still further aspect of the invention provides a polynucleotide which is capable of hybridising to a polynucleotide which encodes fibronectin but not a polynucleotide which encodes the polypeptide whose sequence is (SEQ ID NO:1)

NLVATCLPVRASLPHRLN
MLRGPGPGLLLLAVQCLGTAVPSTGASKSK
RQAQQMVQPQSPVAVSQSKPGCYDNGKHYQ
INQQWERTYLGNALVCTCYGGSRGFNCESK
PEAEETCFDKYTGNTYRVGDTYERPKDSMI
WDCTCIGAGRGRISCTIANRCHEGGQSYKI
GDTWRRPHETGGYMLECVCLGNGKGEWTCK
PIAEKCFDHAAGTSYVVGETWEKPYQGWMM
VDCTCLGEGSGRITCTSRNRCNDQDTRTSY
RIGDTWSKKDNRGNLLQCICTGNGRGEWKC

-continued

```
E R H T S V Q T T S S G S G P F T D V R A A V Y Q P Q H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
C T C V G N G R G E W T C I A Y S Q L R D Q C I V D D I T Y
N V N D T F H K R H E E G H M L N C T C F G Q G R G R W K C
D P V D Q C Q D S E T G T F Y Q I G D S W E K Y V H G V R Y
Q C Y C Y G R G I G E W H C Q P L Q T Y P S S S G P V E V F
I T E T P S Q P N S H P I Q W N A P Q P S H I S K Y I L R W
R P V S I P P R N L G Y
``` or a natural variant thereof.

A yet still further aspect of the invention provides a polynucleotide which is capable of hybridising to a polynucleotide which encodes the polypeptide which encodes the polypeptide whose sequence is

```
                                                (SEQ ID NO:1)
N L V A T C L P V R A S L P H R L N
M L R G P G P G L L L L A V Q C L G T A V P S T G A S K S K
R Q A Q Q M V Q P Q S P V A V S Q S K P G C Y D N G K H Y Q
I N Q Q W E R T Y L G N A L V C T C Y G G S R G F N C E S K
P E A E E T C F D K Y T G N T Y R V G D T Y E R P K D S M I
W D C T C I G A G R G R I S C T I A N R C H E G G Q S Y K I
G D T W R R P H E T G G Y M L E C V C L G N G K G E W T C K
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N G R G E W K C
E R H T S V Q T T S S G S G P F T D V R A A V Y Q P Q H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
C T C V G N G R G E W T C I A Y S Q L R D Q C I V D D I T Y
N V N D T F H K R H E E G H M L N C T C F G Q G R G R W K C
D P V D Q C Q D S E T G T F Y Q I G D S W E K Y V H G V R Y
Q C Y C Y G R G I G E W H C Q P L Q T Y P S S S G P V E V F
```

-continued
ITETPSQPNSHPIQWNAPQPSHISKYILRW

RPVSIPPRNLGY or a natural variant thereof but not to a polynucleotide which encodes fibronectin.

Such polynucleotides can be designed by reference to FIGS. 1 and 2 and the known sequence of fibronectin (SEQ ID NO: 17) (Kornblihtt et al (1985) *EMBO J.* 4, 1755-1759), and may be synthesised by well known methods such as by chemical synthesis or by using specific primers and template, a DNA amplification technique such as the polymerase chain reaction. The polynucleotide may be any polnucleotide, whether DNA or RNA or a synthetic nucleic acid such as a peptide nucleic acid, provided that it can distinguish polynucleotides which encode MSF and fibronectin as said. It is particularly preferred if the polynucleotide is an oligonucleotide which can serve as a hybridisation probe or as a primer for a nucleic acid amplification system. Thus, the polynucleotide of this aspect of the invention may be an oligonucleotide of at least 10 nucleotides in length, more preferably at least 14 nucleotides in length and still more preferably at least 18 nucleotides in length.

It is particularly preferred that the polynucleotide hybridises to a mRNA (or cDNA) which encodes MSF but does not hybridise to a mRNA (or cDNA) which encodes fibronectin.

It is also particularly preferred that the polynucleotide hybridises to a mRNA (or cDNA) which encodes fibronectin but does not hybridise to a mRNA (or cDNA) which encodes MSF. The nucleotide sequence of MSF cDNA is disclosed herein and the nucleotide sequence of fibronectin is known (for example, see Komblihtt et al (1985) *EMBO J.* 4, 1755-1759). The skilled person can readily design probes which can distinguish MSF and fibronectin mRNAs and cDNAs based on this information. Differences between MSF and fibronectin include a 45 bp deletion from the first type II fibronectin repeat module in MSF, and the unique tail present in MSF.

Preferably, the polynucleotides of the invention are detectably labelled. For example, they may be labelled in such a way that they may be directly or indirectly detected. Conveniently, the polynucleotides are labelled with a radioactive moiety or a coloured moiety or a fluorescent moiety or some other suitable detectable moiety. The polynucleotides may be linked to an enzyme, or they may be linked to biotin (or streptavidin) and detected in a similar way as described for antibodies of the invention.

A further aspect of the invention provides a method of diagnosing cancer the method comprising detecting in a sample from the person to be diagnosed the presence of a polypeptide whose sequence is (SEQ ID NO:1)

N L V A T C L P V R A S L P H R L N

M L R G P G P G L L L L A V Q C L G T A V P S T G A S K S K

R Q A Q Q M V Q P Q S P V A V S Q S K P G C Y D N G K H Y Q

I N Q Q W E R T Y L G N A L V C T C Y G G S R G F N C E S K

P E A E E T C F D K Y T G N T Y R V G D T Y E R P K D S M I

W D C T C I G A G R G R I S C T I A N R C H E G G Q S Y K I

G D T W R R P H E T G G Y M L E C V C L G N G K G E W T C K

P I A E K C F D H A A G T S Y V V G E T W E K P Y Q G W M M

V D C T C L G E G S G R I T C T S R N R C N D Q D T R T S Y

R I G D T W S K K D N R G N L L Q C I C T G N G R G E W K C

E R H T S V Q T T S S G S G P F T D V R A A V Y Q P Q P H P

Q P P P Y G H C V T D S G V V Y S V G M Q W L K T Q G N K Q

M L C T C L G N G V S C Q E T A V T Q T Y G G N S N G E P C

V L P F T Y N D R T D S T T S N Y E Q D Q K Y S F C T D H T

V L V Q T R G G N S N G A L C H F P F L Y N N H N Y T D C T

S E G R R D N M K W C G T T Q N Y D A D Q K F G F C P M A A

H E E I C T T N E G V M Y R I G D Q W D K Q H D M G H M M R

C T C V G N R G E W T C I A Y S Q L R D Q C I V D D I T Y

N V N D T F H K R H E E G H M L N C T C F G Q G R G R W K C

-continued
```
D P V D Q C Q D S E T G T F Y Q I G D S W E K Y V H G V R Y

Q C Y C Y G R G I G E W H C Q P L Q T Y P S S S G P V E V F

I T E T P S Q P N S H P I Q W N A P Q P S H I S K Y I L R W

R P V S I P P R N L G Y
``` or a natural variant or fragment thereof using a reagent which can distinguish said polypeptide from fibronectin.

A still further aspect of the invention provides a method of determining susceptibility to cancer the method comprising detecting in a sample derived from the person to be tested the presence of a polypeptide whose sequence is or a natural variant or fragment thereof using a reagent which can distinguish said polypeptide from fibronectin.

A still further aspect of the invention provides a method of determining the likely outcome of a patient with cancer the method comprising detecting in a sample from the patient the presence of a polypeptide whose sequence is

```
                                                          (SEQ ID NO:1)
N L V A T C L P V R A S L P H R L N

M L R G P G P G L L L L A V Q C L G T A V P S T G A S K S K

R Q A Q Q M V Q P Q S P V A V S Q S K P G C Y D N G K H Y Q

I N Q Q W E R T Y L G N A L V C T C Y G G S R G F N C E S K

P E A E E T C F D K Y T G N T Y R V G D T Y E R P K D S M I

W D C T C I G A G R G R I S C T I A N R C H E G G Q S Y K I

G D T W R R P H E T G G Y M L E C V C L G N G K G E W T C K

P I A E K C F D H A A G T S Y V V G E T W E K P Y Q G W M M

V D C T C L G E G S G R I T C T S R N R C N D Q D T R T S Y

R I G D T W S K K D N R G N L L Q C I C T G N G R G E W K C

E R H T S V Q T T S S G S G P F T D V R A A V Y Q P Q P H P

Q P P P Y G H C V T D S G V V Y S V G M Q W L K T Q G N K Q

M L C T C L G N G V S C Q E T A V T Q T Y G G N S N G E P C

V L P F T Y N D R T D S T T S N Y E Q D Q K Y S F C T D H T

V L V Q T R G G N S N G A L C H F P F L Y N N H N Y T D C T

S E G R R D N M K W C G T T Q N Y D A D Q K F G F C P M A A

H E E I C T T N E G V M Y R I G D Q W D K Q H D M G H M M R

C T C V G N G R G E W T C I A Y S Q L R D Q C I V D D I T Y

N V N D T F H K R H E E G H M L N C T C F G Q G R G R W K C

D P V D Q C Q D S E T G T F Y Q I G D S W E K Y V H G V R Y

Q C Y C Y G R G I G E W H C Q P L Q T Y P S S S G P V E V F

I T E T P S Q P N S H P I Q W N A P Q P S H I S K Y I L R W

R P V S I P P R N L G Y
```

(SEQ ID NO:1)

```
N L V A T C L P V R A S L P H R L N
M L R G P G P G L L L L A V Q C L G T A V P S T G A S K S K
R Q A Q Q M V Q P Q S P V A V S Q S K P G C Y D N G K H Y Q
I N Q Q W E R T Y L G N A L V C T C Y G G S R G F N C E S K
P E A E E T C F D K Y T G N T Y R V G D T Y E R P K D S M I
W D C T C I G A G R G R I S C T I A N R C H E G G Q S Y K I
G D T W R R P H E T G G Y M L E C V C L G N G K G E W T C K
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N R G E W K C
E R H T S V Q T T S S G S G P F T D V R A A V Y Q P Q P H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
C T C V G N R G E W T C I A Y S Q L R D Q C I V D D I T Y
N V N D T F H K R H E E G H M L N C T C F G Q G R G R W K C
D P V D Q C Q D S E T G T F Y Q I G D S W E K Y V H G V R Y
Q C Y C Y G R G I G E W H C Q P L Q T Y P S S S G P V E V F
I T E T P S Q P N S H P I Q W N A P Q P S H I S K Y I L R W
R P V S I P P R N L G Y
``` or a natural variant or fragment thereof using a reagent which can distinguish said polypeptide from fibronectin.

Preferably, the reagent which can distinguish MSF from fibronectin is an antibody as disclosed herein. The use of antibodies to detect specific polypeptides in samples is well known. For example, they can be used in enzyme-linked immunosorbend assays (ELISA) or they may be used in histopathological analysis. It is believed that the presence of MSF indicates an elevated risk of cancer.

MSF may be conveniently measured in suitable body fluids such as serum or urine, or in extracts of tissue, or in the medium used to culture patient derived cells in vitro.

The measurement of MSF is believed to be useful in a number of cancers as discussed above. Antibodies may be used to detect MSF in tissue sections by immunolocalisation. Sub-populations of MSF-producing fibroblasts are present in the normal adult (Irwin et al (1994) *J. Cell Science* 107, 1333-1346; Schor et al (1994) pp 277-298 in Mammary Tumorigenesis and Malignant Progression, Dickson, R. and Lippman, M. (eds), 1994, Kluwer Academic Publishers.

It will be appreciated that, as well as the MSF polypeptide being measured using the methods described herein in diagnosis or prognosis or determination of susceptibility to cancer, it may be desirable to detect MSF mRNA in a suitable sample or it may be desirable to detect any changes in the fibronectin gene which are associated with the production of MSF. Mutations in the MSF cDNA or fibronectin gene may be detected using methods well known in the art.

Thus, a further aspect of the invention provides a method of determining susceptibility to cancer the method comprising detecting in a sample derived from the person to be tested the presence of a polynucleotide encoding a polypeptide whose sequence is (SEQ ID NO:1)

```
N L V A T C L P V R A S L P H R L N
M L R G P G P G L L L L A V Q C L G T A V P S T G A S K S K
R Q A Q Q M V Q P Q S P V A V S Q S K P G C Y D N G K H Y Q
```

```
-continued
I N Q Q W E R T Y L G N A L V C T C Y G G S R G F N C E S K
P E A E E T C F D K Y T G N T Y R V G D T Y E R P K D S M I
W D C T C I G A G R G R I S C T I A N R C H E G G Q S Y K I
G D T W R R P H E T G G Y M L E C V C L G N G K G E W T C K
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N G R G E W K C
E R H T S V Q T T S S G S G P F T D V R A A V Y Q P Q H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
V L V Q T R G G N S N G A L C H F P F L Y N N H N Y T D C T
S E G R R D N M K W C G T T Q N Y D A D Q K F G F C P M A A
H E E I C T T N E G V M Y R I G D Q W D K Q H D M G H M M R
C T C V G N G R G E W T C I A Y S Q L R D Q C I V D D I T Y
N V N D T F H K R H E E G H M L N C T C F G Q G R G R W K C
D P V D Q C Q D S E T G T F Y Q I G D S W E K Y V H G V R Y
Q C Y C Y G R G I G E W H C Q P L Q T Y P S S S G P V E V F
I T E T P S Q P N S H P I Q W N A P Q P S H I S K Y I L R W
R P V S I P P R N L G Y
``` or a natural variant or fragment thereof using a reagent which can distinguish said polynucleotide from a polynucleotide encoding fibronectin.

A still further aspect of the invention provides a method of determining the likely outcome of a patient with cancer the method comprising detecting in a sample from the patient the presence of a polynucleotide encoding a polypeptide whose sequence is (SEQ ID NO:1)
```
N L V A T C L P V R A S L P H R L N
M L R G P G P G L L L L A V Q C L G T A V P S T G A S K S K
R Q A Q Q M V Q P Q S P V A V S Q S K P G C Y D N G K H Y Q
I N Q Q W E R T Y L G N A L V C T C Y G G S R G F N C E S K
P E A E E T C F D K Y T G N T Y R V G D T Y E R P K D S M I
W D C T C I G A G R G R I S C T I A N R C H E G G Q S Y K I
G D T W R R P H E T G G Y M L E C V C L G N G K G E W T C K
P I A E K C F D H A A G T S Y V V G E T W E K P Y Q G W M M
V D C T C L G E G S G R I T C T S R N R C N D Q D T R T S Y
R I G D T W S K K D N R G N L L Q C I C T G N G R G E W K C
E R H T S V Q T T S S G S G P F T D V R A A V Y Q P Q H P
Q P P P Y G H C V T D S G V V Y S V G M Q W L K T Q G N K Q
M L C T C L G N G V S C Q E T A V T Q T Y G G N S N G E P C
V L P F T Y N D R T D S T T S N Y E Q D Q K Y S F C T D H T
```

-continued

```
V L V Q T R G G N S N G A L C H F P F L Y N N H N Y T D C T

S E G R R D N M K W C G T T Q N Y D A D Q K F G F C P M A A

H E E I C T T N E G V M Y R I G D Q W D K Q H D M G H M M R

C T C V G N G R G E W T C I A Y S Q L R D Q C I V D D I T Y

N V N D T F H K R H E E G H M L N C T C F G Q G R G R W K C

D P V D Q C Q D S E T G T F Y Q I G D S W E K Y V H G V R Y

Q C Y C Y G R G I G E W H C Q P L Q T Y P S S S G P V E V F

I T E T P S Q P N S H P I Q W N A P Q P S H I S K Y I L R W

R P V S I P P R N L G Y
``` or a natural variant or fragment thereof using a reagent which can distinguish said polynucleotide from a polynucleotide encoding fibronectin.

Preferably, the reagent which can distinguish the polynucleotide encoding MSF from the polynucleotide encoding fibronectin is a suitable polynucleotide as disclosed herein. Methods of detecting specific nucleic acids in a sample are well known in the art. For example, in situ hybridisation methods which detect mRNA may be used, and northern blotting methods may be used. Dot blots, slot blots and Southern blots may also be used.

Thus, it can be seen that the reagents used in the above methods may be used in the manufacture of a reagent for diagnosing cancer.

It will be appreciated that the antibodies of the invention, and the polynucleotides of the invention, which can distinguish MSF and fibronectin (particularly those which recognise MSF or a nucleic acid encoding MSF, but not fibronectin, or a nucleic acid encoding fibronectin) are useful packaged into diagnostic kits containing said antibodies or polynucleotides and other reagents such as means for labelling the said antibodies or polynucleotides.

The invention also includes a number of therapeutic applications, for example chemoprevention and chemotherapy.

Chemoprevention includes the neutralisation of MSF activity and/or the suppression of inappropriate MSF expression in individuals deemed to be at risk of cancer due to inappropriate MSF production. It may also be desirable to administer inhibitors of MSF. Antibodies directed at MSF may act as inhibitors.

Chemotherapy includes the use of anti-MSF antibodies to target coupled cytotoxins to sites of inappropriate MSF production, and the use of MSF inhibitors as mentioned above.

Antibody-targeted cytotoxins are well known in the art and include antibodies linked to a directly cytotoxic moiety such as ricin or a toxic drug; and antibodies linked to an indirectly cytotoxic moiety such as an enzyme which is able to convert a non-toxic prodrug into a toxic drug. In the latter case, the prodrug as well as the antibody-linked enzyme is administered to the patient.

It is useful to measure MSF in wound fluids since this information may be relevant in terms of predicting the efficiency of the subsequent healing process, including the propensity of the scar. The amount of MSF in wound fluids may be measured using, for example, an MSF-selective antibody of the invention.

Inappropriate expression of MSF may be a feature of several pathological conditions characterised by inflammation, such as rheumatoid arthritis. The measurement of MSF in associated body fluid, such as synovial fluid, may be of clinical utility; other pathological conditions of relevance in this context include fibrotic and periodontal disease.

MSF is believed to be involved in the migration of cells, especially fibroblasts any, in particular, the migration of cells may take place within the wound.

Thus, a further aspect of the invention provides a method of modulating cell migration the method comprising administering an effective amount of a polypeptide of the invention to the site where modulation of cell migration is required.

Typically, the cell whose migration is modulated is a fibroblast. Typically, MSF stimulates the migration of cells such as fibroblasts. Preferably, the site where modulation of cell migration is required is a site within a mammalian body, such as the body of a horse, pig, cow, sheep, cat, dog and the like. Most preferably it is a site within a human body. It is preferred if the site within the body is the site of a wound.

A further aspect of the invention provides a method of healing a wound the method comprising administering to the locality of the wound an effective amount of a polypeptide of the invention.

The invention also includes a method of preventing scarring by administering to the locality of the site where scarring is believed to be likely an effective amount of an MSF polypeptide as described herein or a suitable fragment or variant. Preventing or reducing scarring may be part of the wound-healing process. The MSF polypeptide as described herein or a suitable fragment or variant is believed to be useful in preventing or reducing scarring because it reduces hyaluronic acid formation.

It is preferred if the polypeptide administered is a recombinant polypeptide expressed in a eukaryotic host.

The MSF polypeptide may be administered to the site of cell migration or wound healing by any suitable means. Conveniently, the polypeptide is administered topically. It is particularly preferred if the polypeptide is incorporated within an applied wound dressing such as a collagen mesh. Dressings which are suitable for the incorporation of the polypeptide of the invention are well known in the art and many are commercially available.

Other formulations might involve the incorporation of MSF into an ointment, paste, gel, cream (or equivalent) designed for topical application.

The formulations may conveniently be presented in unit dosage form and may be prepared by any of the methods well known in the art of pharmacy. Such methods include the step of bringing into association the active ingredient (polypeptide of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Application of gene therapy techniques may provide a means of controlling MSF expression.

Any suitable amount of the polypeptide of the invention may be administered. By "suitable amount" we mean an amount which gives the desired biological response and that does not lead to any significantly undesirable effects such as toxicity or the like. Small quantities of MSF, for example less than 1 Tg, may be effective. It is preferred if superficial wounds, such as those to the skin, are treated by the method of the invention.

The invention will now be described in further detail with reference to the following Figures and Examples wherein:

FIG. 1 shows the entire nucleotide sequence of the 2.1 kb insert in clone pMSF1I which contains the MSF cDNA. The start and stop codons are underlined.

FIG. 2 shows the translation of the cDNA sequence shown in FIG. 1 and the alignment of the peptide sequence with that of the gelatin-binding domain of fibronectin. The start and end of the MSF polypeptide are indicated by vertical bars and arrows.

FIG. 3 shows the peptide sequence of MSF (as encoded in the pMSF1I clone) according to its domains. The sequence of pMSF1I is shown grouped according to its domains (cf analysis of fibronectin from Komblihtt et al (1985) *EMBO J.* 4, 1755-1759). Residues are numbered and have been aligned to give optimal homology by introducing gaps (indicated by ^). Identical residues within a type of homology are indicated by a box (A), and stop codons are designated by asterisks (*). Deleted amino acids are indicated by dashed lines (-), and the IGDS sequence is underlined.

Figure 4:
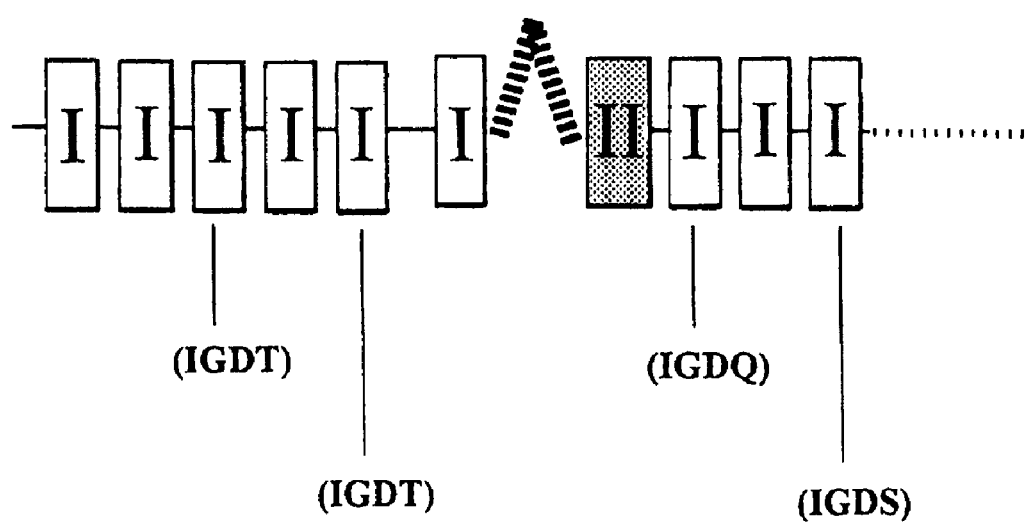

FIG. 4 shows a diagrammatic comparison of fibronectin and MSF.

Figure 5:
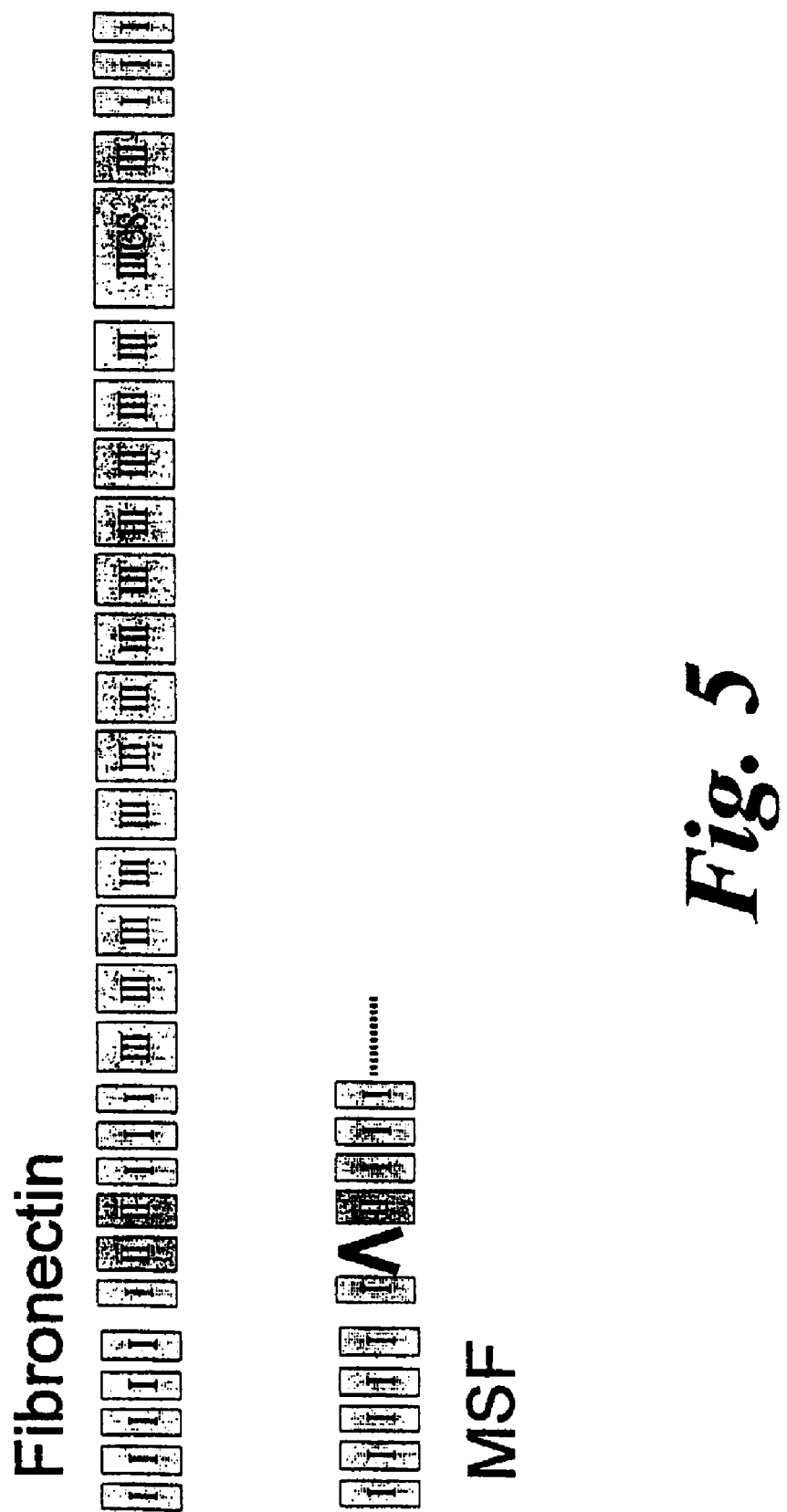

FIG. 5 shows a diagrammatic model of MSF showing the positions of the IGD-containing sequences (ie. IGDT, IGDS and IGDQ) within the domains.

EXAMPLE 1

Cloning and Sequence Analysis of pMSF1I, a Clone Encoding MSF

A cDNA library was constructed using mRNA extracted from a human foetal fibroblast cell line, MRC5-SV2, in the vector λZapII.

A primer based on peptide sequence from the gelatin-binding domain (GBD) of fibronectin was used together with a vector primer in the polymerase chain reaction (PCR) to amplify a fragment of 1.2 kb. Sequence analysis showed a strong homology to GBD for most of the fragment. Clear differences included an internal deletion of 45 bp, and a 3' unique sequence of 175 bp.

The 3' unique sequence was used as a probe for screening the library, using the digoxigenin-labelled system. Positive plaques were picked for further analysis by secondary and tertiary screening, followed by in vivo excision of the pBluescript™ phagemid containing the cloned insert.

A plasmid containing an insert of 2.1 kb, named pMSF1I, was sequenced by the Sanger-dideoxy method, using a progressive priming approach, and the sequence was assembled into a single contain using the Fragment Assembly System of the Daresbury/Seqnet series of programs.

The entire nucleotide sequence of the 2.1 kb fragment is shown in FIG. 1.

Translation of this sequence and alignment of its peptide sequence with that of the gelatin-binding domain of fibronectin was achieved using the Fasta program (Daresbury/Seqnet), and is shown in FIG. 2.

FIG. 3 shows the peptide sequence of pMSF-1I grouped according to its domains.

Other cDNA clones encoding MSF may be readily obtained and sequenced using methods well known in the art and probe derived from the FIG. 1 sequence, in particular probes which distinguish MSF from fibronectin.

EXAMPLE 2

Demonstration of the Presence of MSF-Secreting Fibroblasts in Sections of Breast Cancer, but not Normal Breast Tissue In situ hybridisation using a riboprobe based on the unique coding region for the unique C-terminus of MSF demonstrates the presence of MSF-secreting fibroblasts in sections of breast cancer, but not normal breast tissue.

Suitable riboprobes contain the entire unique nucleotide sequence of MSF-1I (position 1953-2147), and may include up to 10 bases upstream and contained within the fibronectin sequence (position 1943-2152). This ensures high specificity towards MSF-1I, whilst allowing the use of a probe of longer length. A digoxigenin-labelled riboprobe containing a major portion of the unique sequence (position 1974-2147) is used. This region was selected on the basis of the position of convenient restriction sites.

EXAMPLE 3

Monoclonal Antibodies which are Specific to MSF and do not Cross-React with Fibronectin Monoclonal antibodies are raised using any of the currently available standard procedures. The immunogen is a synthetic peptide based on the 10 amino acid unique tail of MSF (VSIPPRNLGY (SEQ ID NO: 41)) or is based on the peptide sequences:

```
ISKYILRWRPVSIPPRNLGY;          (SEQ ID NO: 5)
or

QQWERTYLGNALVCTCYGGSR;         (SEQ ID NO: 6)
or

PCVLPFTYNDRTDSTTSNYEQDQ;       (SEQ ID NO: 7)
or

TDHTVLVQTRGGNSNGALCH;          (SEQ ID NO: 8)
or

VGNGRGEWTCIAYSQLRDQCI          (SEQ ID NO: 9)
```

EXAMPLE 4

Genomic PCR and FISH Studies

Objective: To obtain information regarding the sequence of the genomic MSF gene regarding (i) its relationship to fibronectin, and (ii) chromosomal location.

Background: The 5' upstream untranslated sequence of the cloned MSF cDNA is identical to that of fibronectin, thereby strongly suggesting its close relationship to the fibronectin gene (note: such upstream untranslated regions are virtually never identical between two genes as there is no selective pressure. This inference is in apparent conflict with the "uniqueness" of the 3' end of the MSF cDNA which codes for a 10 amino acid polypeptide and also contains a contiguous untranslated region containing several stop codons).

Methods and Results: Two PCR reactions were established: one at the extreme 5' untranslated region of fibronectin (FN)/MSF and the other at the extreme 3' region of MSF which encompassed the 175 bp unique sequence. Reactions were carried out using DNA purified using the QIAGEN™ Blood kit. Sequence analysis of the resulting amplicon revealed that the 175 bp "unique" sequence was contiguous with the fibronectin sequence.

Experiments were then carried out in order to obtain initial data regarding the genomic location of the 3' unique sequence. This was accomplished by selecting clones from the human PAC library (obtained from HGMP) using the above 2 PCR approach. Secondary and tertiary screening lead to the identification of on which produced products from both PCR reactions. This clone was approximately 70-110 kb in size.

The isolated clone was next subjected to restriction digestion (BamHI and KpnI) and the fragments subcloned into the E. Coli plasmid pBlueScript® and analysed using our 2 PCR approach. Two positive clones were identified: clone B3(2) is 20 kb and can generate both the 5' and 3' fragments, thereby indicating that it contains the entire MSF genomic sequence. The other clone, K5(5) is 7 kb and only contains the 3' unique sequence.

We have used both clones for FISH analysis of the human genome. Our data unambiguously indicate that MSF maps to chromosome 2 region q35. Note: this is within the fibronectin gene, which is located on chromosome 2q34-36.

Conclusions: The FISH analysis clearly indicates that the gene coding for the MSF "unique" sequence is contained within the fibronectin gene. These results indicate that MSF is a novel "mini" splice variant of fibronectin. The genomic fibronectin gene is very large indeed and has still not been fully sequenced. To our knowledge, this is the first report of the unique sequence. The absence of the unique sequence in all previously identified isoforms of fibronectin (which are all in excess of 220 kDa compared to 70 kDa for MSF) indicates that it is spliced out of these molecules.

This information is of relevance for several reasons. Firstly, all previously described splice variants of fibronectin have molecular masses in the region of 225 kDa compared with only 70 kDa of MSF. This small size is totally unexpected and prompts us to refer to MSF as a novel "mini" splice variant of fibronectin. Secondly, all known splice variants of fibronectin involve the inclusion/deletion of entire type III repeats or variable regions of the IIICS region (all of which occur at a considerable distance downstream of the termination of MSF, which does not contain any known splice site). Finally, as the unique 3'-sequence of MSF was not hitherto identified, it was not possible to predict that MSF was indeed a splice variant of fibronectin until the above data was obtained from genomic DNA.

EXAMPLE 5

Recombinant MSF Expression

Objective: To express recombinant human MSF (rhMSF) in 3T3 cells.

Methods and Results: 3T3 cells were transfected using the Lipofectamine/Plus system (Gibco), according to the manufacturer's instructions. The plasmid used was pcDNA3.1/hisB/lacZ. The insert sequence contained a sequence encoding a his tail fused to the human MSF cDNA sequence so that a fusion protein with a his tail is expressed. This facilitates purification of the expressed protein. Transfectants were isolated by their selective growth in medium containing 418. One liter of conditioned medium produced by the transfected cells was collected and the fraction containing all the migration stimulating activity obtained by doing a 0-20% ammonium sulphate precipitation. The pellet was resuspended in buffer and the his-tagged rhMSF purified by passage through a ProBond column (Invitrogen) column, all done in accordance with manufacturer's instructions. Approximately 250 Tg of rhMSF were collected from the starting material. The purified protein resulted in a single band of approximately 70 kDa in SDS PAGE. This protein stimulated the migration of target adult fibroblasts and was active at concentrations between 1 pg/ml to 10 ng/ml (ie in precise agreement with previously published data regarding the dose-response of MSF purified from fetal fibroblast conditioned medium).

EXAMPLE 6

Anti-MSF Antibody Production

Objective: To generate polyclonal antibodies to MSF.

Methods: Rabbits were immunised with a 15-mer synthetic peptide based on the C-terminus of MSF: note, this contains the entire 10 amino acid unique sequence and the contiguous 5 amino sequence of fibronectin. The synthetic peptide was coupled to keyhole limpet haemocyanin (KLH) carrier and used to immunise two rabbits with the following protocol: first injection of 10 mg and second injection of 5 mg three weeks later. Serum was collected six weeks after the first injection and purified IgG shown to recognise the synthetic peptide in both dot and Western blots.

Results: We have used the antibody for both Western blots and immunohistochemistry. The former application has (i)

confirmed that rhMSF is recognised by the antibody, and (ii) demonstrated that fetal, but not adult, fibroblasts produce a 70 kDa molecule which is recognised by the antibody and expresses migration stimulating activity when eluted from the PAGE gels.

Polyclonal antibodies were generated against a synthetic peptide incorporating the 10 amino acid "unique" MSF C-terminal sequence. This antibody recognises the unique synthetic peptide (down to 5 ng) and MSF (down to 10 ng) in dot blots; it does not recognise fibronectin or BSA at concentrations up to 4 μg. This antibody has been used to investigate the tissue distribution of MSF; these experiments show that MSF is present in the stromal compartment of fetal skin and is not detectable in adult skin.

The invention claimed is:

1. An isolated recombinant polynucleotide comprising the polynucleotide sequence of SEQ ID NO: 3.

2. An isolated recombinant polynucleotide comprising the polynucleotide sequence set forth in SEQ ID NO: 3 at positions 57 through 1982.

3. A molecule which is a peptide consisting of a sequence selected from the group consisting of SEQ ID NO: 5, SEQ ID NO: 6, SEQ ID NO: 7, SEQ ID NO: 8, and SEQ ID NO: 9.

* * * * *

```
                            SEQUENCE LISTING

<160> NUMBER OF SEQ ID NOS: 41

<210> SEQ ID NO 1
<211> LENGTH: 660
<212> TYPE: PRT
<213> ORGANISM: Homo sapiens

<400> SEQUENCE: 1

Asn Leu Val Ala Thr Cys Leu Pro Val Arg Ala Ser Leu Pro His Arg
 1               5                  10                  15

Leu Asn Met Leu Arg Gly Pro Gly Leu Leu Leu Ala Val
            20                  25                  30

Gln Cys Leu Gly Thr Ala Val Pro Ser Thr Gly Ala Ser Lys Ser Lys
            35                  40                  45

Arg Gln Ala Gln Met Val Gln Pro Gln Ser Pro Val Ala Val Ser
    50                  55                  60

Gln Ser Lys Pro Gly Cys Tyr Asp Asn Gly Lys His Tyr Gln Ile Asn
65                  70                  75                  80

Gln Gln Trp Glu Arg Thr Tyr Leu Gly Asn Ala Leu Val Cys Thr Cys
                85                  90                  95

Tyr Gly Gly Ser Arg Gly Phe Asn Cys Glu Ser Lys Pro Glu Ala Glu
                100                 105                 110

Glu Thr Cys Phe Asp Lys Tyr Thr Gly Asn Thr Tyr Arg Val Gly Asp
            115                 120                 125

Thr Tyr Glu Arg Pro Lys Asp Ser Met Ile Trp Asp Cys Thr Cys Ile
    130                 135                 140

Gly Ala Gly Arg Gly Arg Ile Ser Cys Thr Ile Ala Asn Arg Cys His
145                 150                 155                 160

Glu Gly Gly Gln Ser Tyr Lys Ile Gly Asp Thr Trp Arg Arg Pro His
                165                 170                 175

Glu Thr Gly Gly Tyr Met Leu Glu Cys Val Cys Leu Gly Asn Gly Lys
                180                 185                 190

Gly Glu Trp Thr Cys Lys Pro Ile Ala Glu Lys Cys Phe Asp His Ala
            195                 200                 205

Ala Gly Thr Ser Tyr Val Val Gly Glu Thr Trp Glu Lys Pro Tyr Gln
    210                 215                 220

Gly Trp Met Met Val Asp Cys Thr Cys Leu Gly Glu Gly Ser Gly Arg
225                 230                 235                 240

Ile Thr Cys Thr Ser Arg Asn Arg Cys Asn Asp Gln Asp Thr Arg Thr
                245                 250                 255

Ser Tyr Arg Ile Gly Asp Thr Trp Ser Lys Lys Asp Asn Arg Gly Asn
                260                 265                 270

Leu Leu Gln Cys Ile Cys Thr Gly Asn Gly Arg Gly Glu Trp Lys Cys
            275                 280                 285

Glu Arg His Thr Ser Val Gln Thr Thr Ser Ser Gly Ser Gly Pro Phe
    290                 295                 300
```

```
Thr Asp Val Arg Ala Ala Val Tyr Gln Pro Gln Pro His Pro Gln Pro
305                 310                 315                 320

Pro Pro Tyr Gly His Cys Val Thr Asp Ser Gly Val Val Tyr Ser Val
            325                 330                 335

Gly Met Gln Trp Leu Lys Thr Gln Gly Asn Lys Gln Met Leu Cys Thr
                340                 345                 350

Cys Leu Gly Asn Gly Val Ser Cys Gln Glu Thr Ala Val Thr Gln Thr
            355                 360                 365

Tyr Gly Gly Asn Ser Asn Gly Glu Pro Cys Val Leu Pro Phe Thr Tyr
        370                 375                 380

Asn Asp Arg Thr Asp Ser Thr Thr Ser Asn Tyr Glu Gln Asp Gln Lys
385                 390                 395                 400

Tyr Ser Phe Cys Thr Asp His Thr Val Leu Val Gln Thr Arg Gly Gly
                405                 410                 415

Asn Ser Asn Gly Ala Leu Cys His Phe Pro Phe Leu Tyr Asn Asn His
            420                 425                 430

Asn Tyr Thr Asp Cys Thr Ser Glu Gly Arg Arg Asp Asn Met Lys Trp
        435                 440                 445

Cys Gly Thr Thr Gln Asn Tyr Asp Ala Asp Gln Lys Phe Gly Phe Cys
    450                 455                 460

Pro Met Ala Ala His Glu Glu Ile Cys Thr Thr Asn Glu Gly Val Met
465                 470                 475                 480

Tyr Arg Ile Gly Asp Gln Trp Asp Lys Gln His Asp Met Gly His Met
                485                 490                 495

Met Arg Cys Thr Cys Val Gly Asn Gly Arg Gly Glu Trp Thr Cys Ile
            500                 505                 510

Ala Tyr Ser Gln Leu Arg Asp Gln Cys Ile Val Asp Asp Ile Thr Tyr
        515                 520                 525

Asn Val Asn Asp Thr Phe His Lys Arg His Glu Glu Gly His Met Leu
    530                 535                 540

Asn Cys Thr Cys Phe Gly Gln Gly Arg Gly Arg Trp Lys Cys Asp Pro
545                 550                 555                 560

Val Asp Gln Cys Gln Asp Ser Glu Thr Gly Thr Phe Tyr Gln Ile Gly
                565                 570                 575

Asp Ser Trp Glu Lys Tyr Val His Gly Val Arg Tyr Gln Cys Tyr Cys
            580                 585                 590

Tyr Gly Arg Gly Ile Gly Glu Trp His Cys Gln Pro Leu Gln Thr Tyr
        595                 600                 605

Pro Ser Ser Ser Gly Pro Val Glu Val Phe Ile Thr Glu Thr Pro Ser
    610                 615                 620

Gln Pro Asn Ser His Pro Ile Gln Trp Asn Ala Pro Gln Pro Ser His
625                 630                 635                 640

Ile Ser Lys Tyr Ile Leu Arg Trp Arg Pro Val Ser Ile Pro Pro Arg
                645                 650                 655

Asn Leu Gly Tyr
            660

<210> SEQ ID NO 2
<211> LENGTH: 642
<212> TYPE: PRT
<213> ORGANISM: Homo sapiens

<400> SEQUENCE: 2

Met Leu Arg Gly Pro Gly Pro Gly Leu Leu Leu Leu Ala Val Gln Cys
1               5                   10                  15
```

-continued

```
Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
 50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
             100                 105                 110

Glu Arg Pro Lys Asp Ser Met Ile Trp Asp Cys Thr Cys Ile Gly Ala
         115                 120                 125

Gly Arg Gly Arg Ile Ser Cys Thr Ile Ala Asn Arg Cys His Glu Gly
     130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                 165                 170                 175

Trp Thr Cys Lys Pro Ile Ala Glu Lys Cys Phe Asp His Ala Ala Gly
             180                 185                 190

Thr Ser Tyr Val Val Gly Glu Thr Trp Glu Lys Pro Tyr Gln Gly Trp
         195                 200                 205

Met Met Val Asp Cys Thr Cys Leu Gly Glu Gly Ser Gly Arg Ile Thr
     210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                 245                 250                 255

Gln Cys Ile Cys Thr Gly Asn Gly Arg Gly Glu Trp Lys Cys Glu Arg
             260                 265                 270

His Thr Ser Val Gln Thr Thr Ser Ser Gly Ser Gly Pro Phe Thr Asp
         275                 280                 285

Val Arg Ala Ala Val Tyr Gln Pro Gln Pro His Pro Gln Pro Pro
     290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                 325                 330                 335

Gly Asn Gly Val Ser Cys Gln Glu Thr Ala Val Thr Gln Thr Tyr Gly
             340                 345                 350

Gly Asn Ser Asn Gly Glu Pro Cys Val Leu Pro Phe Thr Tyr Asn Asp
         355                 360                 365

Arg Thr Asp Ser Thr Thr Ser Asn Tyr Glu Gln Asp Gln Lys Tyr Ser
     370                 375                 380

Phe Cys Thr Asp His Thr Val Leu Val Gln Thr Arg Gly Gly Asn Ser
385                 390                 395                 400

Asn Gly Ala Leu Cys His Phe Pro Phe Leu Tyr Asn Asn His Asn Tyr
                 405                 410                 415

Thr Asp Cys Thr Ser Glu Gly Arg Arg Asp Asn Met Lys Trp Cys Gly
             420                 425                 430
```

```
Thr Thr Gln Asn Tyr Asp Ala Asp Gln Lys Phe Gly Phe Cys Pro Met
        435                 440                 445
Ala Ala His Glu Glu Ile Cys Thr Thr Asn Glu Gly Val Met Tyr Arg
    450                 455                 460
Ile Gly Asp Gln Trp Asp Lys Gln His Asp Met Gly His Met Met Arg
465                 470                 475                 480
Cys Thr Cys Val Gly Asn Gly Arg Gly Glu Trp Thr Cys Ile Ala Tyr
                485                 490                 495
Ser Gln Leu Arg Asp Gln Cys Ile Val Asp Asp Ile Thr Tyr Asn Val
            500                 505                 510
Asn Asp Thr Phe His Lys Arg His Glu Glu Gly His Met Leu Asn Cys
        515                 520                 525
Thr Cys Phe Gly Gln Gly Arg Gly Arg Trp Lys Cys Asp Pro Val Asp
    530                 535                 540
Gln Cys Gln Asp Ser Glu Thr Gly Thr Phe Tyr Gln Ile Gly Asp Ser
545                 550                 555                 560
Trp Glu Lys Tyr Val His Gly Val Arg Tyr Gln Cys Tyr Cys Tyr Gly
                565                 570                 575
Arg Gly Ile Gly Glu Trp His Cys Gln Pro Leu Gln Thr Tyr Pro Ser
            580                 585                 590
Ser Ser Gly Pro Val Glu Val Phe Ile Thr Glu Thr Pro Ser Gln Pro
        595                 600                 605
Asn Ser His Pro Ile Gln Trp Asn Ala Pro Gln Pro Ser His Ile Ser
    610                 615                 620
Lys Tyr Ile Leu Arg Trp Arg Pro Val Ser Ile Pro Pro Arg Asn Leu
625                 630                 635                 640

Gly Tyr

<210> SEQ ID NO 3
<211> LENGTH: 2147
<212> TYPE: DNA
<213> ORGANISM: Homo sapiens

<400> SEQUENCE: 3
caaacttggt ggcaacttgc ctcccggtgc gggcgtctct cccccaccgt ctcaacatgc      60
ttaggggtcc ggggcccggg ctgctgctgc tggccgtcca gtgcctgggg acagcggtgc     120
cctccacggg agcctcgaag agcaagaggc aggctcagca aatggttcag ccccagtccc     180
cggtggctgt cagtcaaagc aagcccggtt gttatgacaa tggaaaacac tatcagataa     240
atcaacagtg ggagcggacc tacctaggca atgcgttggt ttgtacttgt atggaggaa     300
gccgaggttt taactgcgag agtaaacctg aagctgaaga gacttgcttt gacaagtaca     360
ctgggaacac ttaccgagtg gtgacacttt atgagcgtcc taaagactcc atgatctggg     420
actgtaccto catcggggct gggcgaggga aataagctg taccatcgca aaccgctgcc     480
atgaagggg tcagtcctac aagattggtg acacctggag agaccacat gagactggtg     540
gttacatgtt agagtgtgtg tgtcttggta atggaaaagg agaatggacc tgcaagccca     600
tagctgagaa gtgttttgat catgctgctg ggacttccta tgtggtcgga gaaacgtggg     660
agaagcccta ccaaggctgg atgatggtag attgtacttg cctgggagaa ggcagcggac     720
gcatcacttg cacttctaga aatagatgca acgatcagga cacaaggaca tcctatagaa     780
ttggagacac ctggagcaag aaggataatc gaggaaacct gctccagtgc atctgcacag     840
gcaacggccg aggagagtgg aagtgtgaga ggcacacctc tgtgcagacc acatcgagcg     900
```

| | |
|---|---:|
| gatctggccc cttcaccgat gttcgtgcag ctgtttacca accgcagcct cacccccagc | 960 |
| ctcctcccta tggccactgt gtcacagaca gtggtgtggt ctactctgtg gggatgcagt | 1020 |
| ggctgaagac acaaggaaat aagcaaatgc tttgcacgtg cctgggcaac ggagtcagct | 1080 |
| gccaagagac agctgtaacc cagacttacg gtggcaactc aaatggagag ccatgtgtct | 1140 |
| taccattcac ctacaacgac aggacggaca gcacaacttc gaattatgag caggaccaga | 1200 |
| aatactcttt ctgcacagac cacactgttt tggttcagac tcgaggagga aattccaatg | 1260 |
| gtgccttgtg ccacttcccc ttcctataca acaaccacaa ttacactgat tgcacttctg | 1320 |
| agggcagaag agacaacatg aagtggtgtg ggaccacaca gaactatgat gccgaccaga | 1380 |
| agtttgggtt ctgccccatg gctgcccacg aggaaatctg cacaaccaat gaagggggtca | 1440 |
| tgtaccgcat tggagatcag tgggataagc agcatgacat gggtcacatg atgaggtgca | 1500 |
| cgtgtgttgg gaatggtcgt ggggaatgga catgcattgc ctactcgcag cttcgagatc | 1560 |
| agtgcattgt tgatgacatc acttacaatg tgaacgcac attccacaag cgtcatgaag | 1620 |
| aggggcacat gctgaactgt acatgcttcg gtcagggtcg gggcaggtgg aagtgtgatc | 1680 |
| ccgtcgacca atgccaggat tcagagactg ggacgtttta tcaaattgga gattcatggg | 1740 |
| agaagtatgt gcatggtgtc agataccagt gctactgcta tggccgtggc attggggagt | 1800 |
| ggcattgcca accttacag acctatccaa gctcaagtgg tcctgtcgaa gtatttatca | 1860 |
| ctgagactcc gagtcagccc aactcccacc ccatccagtg gaatgcacca cagccatctc | 1920 |
| acatttccaa gtacattctc aggtggagac ctgtgagtat cccacccaga aaccttggat | 1980 |
| actgagtctc ctaatcttat caattctgat ggtttctttt tttcccagct tttgagccaa | 2040 |
| caactctgat taactattcc tatagcattt actatatttg tttagtgaac aaacaatatg | 2100 |
| tggtcaatta aattgacttg tagactgaaa aaaaaaaaaa aaaaaaa | 2147 |

<210> SEQ ID NO 4
<211> LENGTH: 1929
<212> TYPE: DNA
<213> ORGANISM: Homo sapiens

<400> SEQUENCE: 4

| | |
|---|---:|
| atgcttaggg gtccggggcc cgggctgctg ctgctggccg tccagtgcct ggggacagcg | 60 |
| gtgccctcca cgggagcctc gaagagcaag aggcaggctc agcaaatggt tcagccccag | 120 |
| tccccggtgg ctgtcagtca aagcaagccc ggttgttatg acaatggaaa acactatcag | 180 |
| ataaatcaac agtgggagcg gacctaccta ggcaatgcgt tggtttgtac ttgttatgga | 240 |
| ggaagccgag gttttaactg cgagagtaaa cctgaagctg aagagacttg ctttgacaag | 300 |
| tacactggga acacttaccg agtgggtgac acttatgagc gtcctaaaga ctccatgatc | 360 |
| tgggactgta cctgcatcgg ggctgggcga gggagaataa gctgtaccat cgcaaaccgc | 420 |
| tgccatgaag gggtcagtc ctacaagatt ggtgacacct ggaggagacc acatgagact | 480 |
| ggtggttaca tgttagagtg tgtgtgtctt ggtaatggaa aaggagaatg gacctgcaag | 540 |
| cccatagctg agaagtgttt tgatcatgct gctgggactt cctatgtggt cggagaaacg | 600 |
| tgggagaagc cctaccaagg ctggatgatg gtagattgta cttgcctggg agaaggcagc | 660 |
| ggacgcatca cttgcacttc tagaaataga tgcaacgatc aggacacaag gacatcctat | 720 |
| agaattggag acacctggag caagaaggat aatcgaggaa acctgctcca gtgcatctgc | 780 |
| acaggcaacg gccgaggaga gtggaagtgt gagaggcaca cctctgtgca gaccacatcg | 840 |
| agcggatctg gccccttcac cgatgttcgt gcagctgttt accaaccgca gcctcacccc | 900 |

```
cagcctcctc cctatggcca ctgtgtcaca gacagtggtg tggtctactc tgtggggatg      960
cagtggctga agacacaagg aaataagcaa atgctttgca cgtgcctggg caacggagtc     1020
agctgccaag agacagctgt aacccagact tacggtggca actcaaatgg agagccatgt     1080
gtcttaccat tcacctacaa cgacaggacg gacagcacaa cttcgaatta tgagcaggac     1140
cagaaatact ctttctgcac agaccacact gttttggttc agactcgagg aggaaattcc     1200
aatggtgcct tgtgccactt cccttccta tacaacaacc acaattacac tgattgcact     1260
tctgagggca aagagacaa catgaagtgg tgtgggacca cagaactact tgatgccgac     1320
cagaagtttg ggttctgccc catggctgcc cacgaggaaa tctgcacaac caatgaaggg     1380
gtcatgtacc gcattggaga tcagtgggat aagcagcatg acatgggtca catgatgagg     1440
tgcacgtgtg ttgggaatgg tcgtggggaa tggacatgca ttgcctactc gcagcttcga     1500
gatcagtgca ttgttgatga catcacttac aatgtgaacg acacattcca caagcgtcat     1560 gaagagggc acatgctgaa ctgtacatgc ttcggtcagg gtcggggcag gtggaagtgt     1620
gatcccgtcg accaatgcca ggattcagag actgggacgt ttatcaaat tggagattca     1680 tgggagaagt atgtgcatgg tgtcagatac cagtgctact gctatggccg tggcattggg     1740
gagtggcatt gccaaccttt acagacctat ccaagctcaa gtggtcctgt cgaagtattt     1800
atcactgaga ctccgagtca gcccaactcc cacccatcc agtggaatgc accacagcca     1860
tctcacattt ccaagtacat tctcaggtgg agacctgtga gtatcccacc cagaaaccct     1920
ggatactga                                                              1929
```

<210> SEQ ID NO 5
<211> LENGTH: 20
<212> TYPE: PRT
<213> ORGANISM: Homo sapiens

<400> SEQUENCE: 5

Ile Ser Lys Tyr Ile Leu Arg Trp Arg Pro Val Ser Ile Pro Pro Arg
 1               5                  10                  15
Asn Leu Gly Tyr
         20

<210> SEQ ID NO 6
<211> LENGTH: 21
<212> TYPE: PRT
<213> ORGANISM: Homo sapiens

<400> SEQUENCE: 6

Gln Gln Trp Glu Arg Thr Tyr Leu Gly Asn Ala Leu Val Cys Thr Cys
 1               5                  10                  15
Tyr Gly Gly Ser Arg
         20

<210> SEQ ID NO 7
<211> LENGTH: 23
<212> TYPE: PRT
<213> ORGANISM: Homo sapiens

<400> SEQUENCE: 7

Pro Cys Val Leu Pro Phe Thr Tyr Asn Asp Arg Thr Asp Ser Thr Thr
 1               5                  10                  15
Ser Asn Tyr Glu Gln Asp Gln
         20

-continued

```
<210> SEQ ID NO 8
<211> LENGTH: 20
<212> TYPE: PRT
<213> ORGANISM: Homo sapiens

<400> SEQUENCE: 8

Thr Asp His Thr Val Leu Val Gln Thr Arg Gly Gly Asn Ser Asn Gly
1               5                   10                  15

Ala Leu Cys His
            20

<210> SEQ ID NO 9
<211> LENGTH: 21
<212> TYPE: PRT
<213> ORGANISM: Homo sapiens

<400> SEQUENCE: 9

Val Gly Asn Gly Arg Gly Glu Trp Thr Cys Ile Ala Tyr Ser Gln Leu
1               5                   10                  15

Arg Asp Gln Cys Ile
            20

<210> SEQ ID NO 10
<211> LENGTH: 21
<212> TYPE: PRT
<213> ORGANISM: Homo sapiens

<400> SEQUENCE: 10

Gln Gln Trp Glu Arg Thr Tyr Leu Gly Asn Val Leu Val Cys Thr Cys
1               5                   10                  15

Tyr Gly Gly Ser Arg
            20

<210> SEQ ID NO 11
<211> LENGTH: 39
<212> TYPE: PRT
<213> ORGANISM: Homo sapiens

<400> SEQUENCE: 11

Glu Pro Cys Val Leu Pro Phe Thr Tyr Asn Gly Arg Thr Phe Tyr Ser
1               5                   10                  15

Cys Thr Thr Glu Gly Arg Gln Asp Gly His Leu Trp Cys Ser Thr Thr
            20                  25                  30

Ser Asn Tyr Glu Gln Asp Gln
        35

<210> SEQ ID NO 12
<211> LENGTH: 21
<212> TYPE: PRT
<213> ORGANISM: Homo sapiens

<400> SEQUENCE: 12

Cys Thr Asp His Thr Val Leu Val Gln Thr Gln Gly Gly Asn Ser Asn
1               5                   10                  15

Gly Ala Leu Cys His
            20

<210> SEQ ID NO 13
<211> LENGTH: 21
<212> TYPE: PRT
<213> ORGANISM: Homo sapiens
```

```
<400> SEQUENCE: 13

Val Gly Asn Gly Arg Gly Glu Trp Thr Cys Tyr Ala Tyr Ser Gln Leu
1               5                   10                  15

Arg Asp Gln Cys Ile
            20

<210> SEQ ID NO 14
<211> LENGTH: 20
<212> TYPE: PRT
<213> ORGANISM: Homo sapiens

<400> SEQUENCE: 14

Ile Ser Lys Tyr Ile Leu Arg Trp Arg Pro Lys Asn Ser Val Gly Arg
1               5                   10                  15

Trp Lys Glu Ala
            20

<210> SEQ ID NO 15
<211> LENGTH: 56
<212> TYPE: PRT
<213> ORGANISM: Homo sapiens

<400> SEQUENCE: 15

Pro Lys Asn Ser Val Gly Arg Trp Lys Glu Ala Thr Ile Pro Gly His
1               5                   10                  15

Leu Asn Ser Tyr Thr Ile Lys Gly Leu Lys Pro Gly Val Val Tyr Glu
                20                  25                  30

Gly Gln Leu Ile Ser Ile Gln Gln Tyr Gly His Gln Glu Val Thr Arg
            35                  40                  45

Phe Asp Phe Thr Thr Thr Ser Thr
        50                  55

<210> SEQ ID NO 16
<211> LENGTH: 11
<212> TYPE: PRT
<213> ORGANISM: Homo sapiens

<400> SEQUENCE: 16

Thr Ala Ser Gly Val Ala Glu Thr Thr Asn Cys
1               5                   10

<210> SEQ ID NO 17
<211> LENGTH: 720
<212> TYPE: PRT
<213> ORGANISM: Homo sapiens

<400> SEQUENCE: 17

Asn Leu Val Ala Thr Cys Leu Pro Val Arg Ala Ser Leu Pro His Arg
1               5                   10                  15

Leu Asn Met Leu Arg Gly Pro Gly Pro Gly Leu Leu Leu Leu Ala Val
                20                  25                  30

Leu Cys Leu Gly Thr Ala Val Pro Ser Thr Gly Ala Ser Lys Ser Lys
            35                  40                  45

Arg Gln Ala Gln Gln Met Val Gln Pro Gln Ser Pro Val Ala Val Ser
        50                  55                  60

Gln Ser Lys Pro Gly Cys Tyr Asp Asn Gly Lys His Tyr Gln Ile Asn
65                  70                  75                  80

Gln Gln Trp Glu Arg Thr Tyr Leu Gly Asn Val Leu Val Cys Thr Cys
                85                  90                  95
```

-continued

```
Tyr Gly Gly Ser Arg Gly Phe Asn Cys Glu Ser Lys Pro Glu Ala Glu
            100                 105                 110

Glu Thr Cys Phe Asp Lys Tyr Thr Gly Asn Thr Tyr Arg Val Gly Asp
                115                 120                 125

Thr Tyr Glu Arg Pro Lys Asp Ser Met Ile Trp Asp Cys Thr Cys Ile
        130                 135                 140

Gly Ala Gly Arg Gly Arg Ile Ser Cys Thr Ile Ala Asn Arg Cys His
145                 150                 155                 160

Glu Gly Gly Gln Ser Tyr Lys Ile Gly Asp Thr Trp Arg Arg Pro His
                165                 170                 175

Glu Thr Gly Gly Tyr Met Leu Glu Cys Val Cys Leu Gly Asn Gly Lys
                180                 185                 190

Gly Glu Trp Thr Cys Lys Pro Ile Ala Glu Lys Cys Phe Asp His Ala
            195                 200                 205

Ala Gly Thr Ser Tyr Val Val Gly Glu Thr Trp Glu Lys Pro Tyr Gln
        210                 215                 220

Gly Trp Met Met Val Asp Cys Thr Cys Leu Gly Glu Gly Ser Gly Arg
225                 230                 235                 240

Ile Thr Cys Thr Ser Arg Asn Arg Cys Asn Asp Gln Asp Thr Arg Thr
                245                 250                 255

Ser Tyr Arg Ile Gly Asp Thr Trp Ser Lys Lys Asp Asn Arg Gly Asn
            260                 265                 270

Leu Leu Gln Cys Ile Cys Thr Gly Asn Gly Arg Gly Glu Trp Lys Cys
                275                 280                 285

Glu Arg His Thr Ser Val Gln Thr Thr Ser Ser Gly Ser Gly Pro Phe
            290                 295                 300

Thr Asp Val Arg Ala Ala Val Tyr Gln Pro Gln Pro His Pro Gln Pro
305                 310                 315                 320

Pro Pro Tyr Gly His Cys Val Thr Asp Ser Gly Val Val Tyr Ser Val
                325                 330                 335

Gly Met Gln Trp Leu Lys Thr Gln Gly Asn Lys Gln Met Leu Cys Thr
            340                 345                 350

Cys Leu Gly Asn Gly Val Ser Cys Gln Glu Thr Ala Val Thr Gln Thr
            355                 360                 365

Tyr Gly Gly Asn Ser Asn Gly Glu Pro Cys Val Leu Pro Phe Thr Tyr
        370                 375                 380

Asn Gly Arg Thr Phe Tyr Ser Cys Thr Thr Glu Gly Arg Gln Asp Gly
385                 390                 395                 400

His Leu Trp Cys Ser Thr Thr Ser Asn Tyr Glu Gln Asp Gln Lys Tyr
                405                 410                 415

Ser Phe Cys Thr Asp His Thr Val Leu Val Gln Thr Gln Gly Gly Asn
            420                 425                 430

Ser Asn Gly Ala Leu Cys His Phe Pro Phe Leu Tyr Asn Asn His Asn
        435                 440                 445

Tyr Thr Asp Cys Thr Ser Glu Gly Arg Arg Asp Asn Met Lys Trp Cys
        450                 455                 460

Gly Thr Thr Gln Asn Tyr Asp Ala Asp Gln Lys Phe Gly Phe Cys Pro
465                 470                 475                 480

Met Ala Ala His Glu Glu Ile Cys Thr Thr Asn Glu Gly Val Met Tyr
                485                 490                 495

Arg Ile Gly Asp Gln Trp Asp Lys Gln His Asp Met Gly His Met Met
            500                 505                 510

Arg Cys Thr Cys Val Gly Asn Gly Arg Gly Glu Trp Thr Cys Tyr Ala
```

```
                515                 520                 525
Tyr Ser Gln Leu Arg Asp Gln Cys Ile Val Asp Asp Ile Thr Tyr Asn
        530                 535                 540

Val Asn Asp Thr Phe His Lys Arg His Glu Glu Gly His Met Leu Asn
545                 550                 555                 560

Cys Thr Cys Phe Gly Gln Gly Arg Gly Arg Trp Lys Cys Asp Pro Val
                565                 570                 575

Asp Gln Cys Gln Asp Ser Glu Thr Gly Thr Phe Tyr Gln Ile Gly Asp
                580                 585                 590

Ser Trp Glu Lys Tyr Val His Gly Val Arg Tyr Gln Cys Tyr Cys Tyr
                595                 600                 605

Gly Arg Gly Ile Gly Glu Trp His Cys Gln Pro Leu Gln Thr Tyr Pro
        610                 615                 620

Ser Ser Ser Gly Pro Val Glu Val Phe Ile Thr Glu Thr Pro Ser Gln
625                 630                 635                 640

Pro Asn Ser His Pro Ile Gln Trp Asn Ala Pro Gln Pro Ser His Ile
                645                 650                 655

Ser Lys Tyr Ile Leu Arg Trp Arg Pro Lys Asn Ser Val Gly Arg Trp
                660                 665                 670

Lys Glu Ala Thr Ile Pro Gly His Leu Asn Ser Tyr Thr Ile Lys Gly
                675                 680                 685

Leu Lys Pro Gly Val Val Tyr Glu Gly Gln Leu Ile Ser Ile Gln Gln
        690                 695                 700

Tyr Gly His Gln Glu Val Thr Arg Phe Asp Phe Thr Thr Thr Ser Thr
705                 710                 715                 720

<210> SEQ ID NO 18
<211> LENGTH: 703
<212> TYPE: PRT
<213> ORGANISM: Homo sapiens
<220> FEATURE:
<221> NAME/KEY: VARIANT
<222> LOCATION: 660, 663, 667, 701
<223> OTHER INFORMATION: Xaa = Any Amino Acid

<400> SEQUENCE: 1

Asn Leu Val Ala Thr Cys Leu Pro Val Arg Ala Ser Leu Pro His Arg
1               5                   10                  15

Leu Asn Met Leu Arg Gly Pro Gly Pro Gly Leu Leu Leu Leu Ala Val
                20                  25                  30

Leu Cys Leu Gly Thr Ala Val Pro Ser Thr Gly Ala Ser Lys Ser Lys
            35                  40                  45

Arg Gln Ala Gln Gln Met Val Gln Pro Gln Ser Pro Val Ala Val Ser
50                  55                  60

Gln Ser Lys Pro Gly Cys Tyr Asp Asn Gly Lys His Tyr Gln Ile Asn
65                  70                  75                  80

Gln Gln Trp Glu Arg Thr Tyr Leu Gly Asn Val Leu Val Cys Thr Cys
                85                  90                  95

Tyr Gly Gly Ser Arg Gly Phe Asn Cys Glu Ser Lys Pro Glu Ala Glu
                100                 105                 110

Glu Thr Cys Phe Asp Lys Tyr Thr Gly Asn Thr Tyr Arg Val Gly Asp
            115                 120                 125

Thr Tyr Glu Arg Pro Lys Asp Ser Met Ile Trp Asp Cys Thr Cys Ile
130                 135                 140

Gly Ala Gly Arg Gly Arg Ile Ser Cys Thr Ile Ala Asn Arg Cys His
145                 150                 155                 160
```

-continued

```
Glu Gly Gly Gln Ser Tyr Lys Ile Gly Asp Thr Trp Arg Arg Pro His
                165                 170                 175
Glu Thr Gly Gly Tyr Met Leu Glu Cys Val Cys Leu Gly Asn Gly Lys
            180                 185                 190
Gly Glu Trp Thr Cys Lys Pro Ile Ala Glu Lys Cys Phe Asp His Ala
        195                 200                 205
Ala Gly Thr Ser Tyr Val Val Gly Glu Thr Trp Glu Lys Pro Tyr Gln
    210                 215                 220
Gly Trp Met Met Val Asp Cys Thr Cys Leu Gly Glu Gly Ser Gly Arg
225                 230                 235                 240
Ile Thr Cys Thr Ser Arg Asn Arg Cys Asn Asp Gln Asp Thr Arg Thr
                245                 250                 255
Ser Tyr Arg Ile Gly Asp Thr Trp Ser Lys Lys Asp Asn Arg Gly Asn
            260                 265                 270
Leu Leu Gln Cys Ile Cys Thr Gly Asn Gly Arg Gly Glu Trp Lys Cys
        275                 280                 285
Glu Arg His Thr Ser Val Gln Thr Thr Ser Ser Gly Ser Gly Pro Phe
    290                 295                 300
Thr Asp Val Arg Ala Ala Val Tyr Gln Pro Gln Pro His Pro Gln Pro
305                 310                 315                 320
Pro Pro Tyr Gly His Cys Val Thr Asp Ser Gly Val Val Tyr Ser Val
                325                 330                 335
Gly Met Gln Trp Leu Lys Thr Gln Gly Asn Lys Gln Met Leu Cys Thr
            340                 345                 350
Cys Leu Gly Asn Gly Val Ser Cys Gln Glu Thr Ala Val Thr Gln Thr
        355                 360                 365
Tyr Gly Gly Asn Ser Asn Gly Glu Pro Cys Val Leu Pro Phe Thr Tyr
    370                 375                 380
Asn Gly Arg Thr Ser Thr Thr Ser Asn Tyr Glu Gln Asp Gln Lys Tyr
385                 390                 395                 400
Ser Phe Cys Thr Asp His Thr Val Leu Val Gln Thr Gln Gly Gly Asn
                405                 410                 415
Ser Asn Gly Ala Leu Cys His Phe Pro Phe Leu Tyr Asn Asn His Asn
            420                 425                 430
Tyr Thr Asp Cys Thr Ser Glu Gly Arg Arg Asp Asn Met Lys Trp Cys
        435                 440                 445
Gly Thr Thr Gln Asn Tyr Asp Ala Asp Gln Lys Phe Gly Phe Cys Pro
    450                 455                 460
Met Ala Ala His Glu Glu Ile Cys Thr Thr Asn Glu Gly Val Met Tyr
465                 470                 475                 480
Arg Ile Gly Asp Gln Trp Asp Lys Gln His Asp Met Gly His Met Met
                485                 490                 495
Arg Cys Thr Cys Val Gly Asn Gly Arg Gly Glu Trp Thr Cys Tyr Ala
            500                 505                 510
Tyr Ser Gln Leu Arg Asp Gln Cys Ile Val Asp Asp Ile Thr Tyr Asn
        515                 520                 525
Val Asn Asp Thr Phe His Lys Arg His Glu Glu Gly His Met Leu Asn
    530                 535                 540
Cys Thr Cys Phe Gly Gln Gly Arg Gly Arg Trp Lys Cys Asp Pro Val
545                 550                 555                 560
Asp Gln Cys Gln Asp Ser Glu Thr Gly Thr Phe Tyr Gln Ile Gly Asp
                565                 570                 575
```

```
Ser Trp Glu Lys Tyr Val His Gly Val Arg Tyr Gln Cys Tyr Cys Tyr
            580                 585                 590

Gly Arg Gly Ile Gly Glu Trp His Cys Gln Pro Leu Gln Thr Tyr Pro
            595                 600                 605

Ser Ser Ser Gly Pro Val Glu Val Phe Ile Thr Glu Thr Pro Ser Gln
            610                 615                 620

Pro Asn Ser His Pro Ile Gln Trp Asn Ala Pro Gln Pro Ser His Ile
625                 630                 635                 640

Ser Lys Tyr Ile Leu Arg Trp Arg Pro Val Ser Ile Pro Pro Arg Asn
                645                 650                 655

Leu Gly Tyr Xaa Val Ser Xaa Ser Gln Phe Xaa Trp Phe Leu Phe Phe
            660                 665                 670

Pro Ala Phe Glu Pro Thr Thr Leu Ile Asn Tyr Ser Tyr Ser Ile Tyr
            675                 680                 685

Tyr Ile Cys Leu Val Asn Lys Gln Tyr Val Val Asn Xaa Ile Asp
            690                 695                 700

<210> SEQ ID NO 19
<211> LENGTH: 18
<212> TYPE: PRT
<213> ORGANISM: Homo sapiens

<400> SEQUENCE: 19

Asn Leu Val Ala Thr Cys Leu Pro Val Arg Ala Ser Leu Pro His Arg
1               5                   10                  15

Leu Asn

<210> SEQ ID NO 20
<211> LENGTH: 31
<212> TYPE: PRT
<213> ORGANISM: Homo sapiens

<400> SEQUENCE: 20

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg
                20                  25                  30

<210> SEQ ID NO 21
<211> LENGTH: 20
<212> TYPE: PRT
<213> ORGANISM: Homo sapiens

<400> SEQUENCE: 21

Gln Ala Gln Gln Met Val Gln Pro Gln Ser Pro Val Ala Val Ser Gln
1               5                   10                  15

Ser Lys Pro Gly
            20

<210> SEQ ID NO 22
<211> LENGTH: 45
<212> TYPE: PRT
<213> ORGANISM: Homo sapiens

<400> SEQUENCE: 22

Cys Tyr Asp Asn Gly Lys His Tyr Gln Ile Asn Gln Gln Trp Glu Arg
1               5                   10                  15

Thr Tyr Leu Gly Asn Ala Leu Val Cys Thr Cys Tyr Gly Gly Ser Arg
                20                  25                  30
```

```
Gly Phe Asn Cys Glu Ser Lys Pro Glu Ala Glu Glu Thr
        35                  40                  45
```

<210> SEQ ID NO 23
<211> LENGTH: 44
<212> TYPE: PRT
<213> ORGANISM: Homo sapiens

<400> SEQUENCE: 23

```
Cys Phe Asp Lys Tyr Thr Gly Asn Thr Tyr Arg Val Gly Asp Thr Tyr
1               5                   10                  15
Glu Arg Pro Lys Asp Ser Met Ile Trp Asp Cys Thr Cys Ile Gly Ala
            20                  25                  30
Gly Arg Gly Arg Ile Ser Cys Thr Ile Ala Asn Arg
        35                  40
```

<210> SEQ ID NO 24
<211> LENGTH: 45
<212> TYPE: PRT
<213> ORGANISM: Homo sapiens

<400> SEQUENCE: 24

```
Cys His Glu Gly Gly Gln Ser Tyr Lys Ile Gly Asp Thr Trp Arg Arg
1               5                   10                  15
Pro His Glu Thr Gly Gly Tyr Met Leu Glu Cys Val Cys Leu Gly Asn
            20                  25                  30
Gly Lys Gly Glu Trp Thr Cys Lys Pro Ile Ala Glu Lys
        35                  40                  45
```

<210> SEQ ID NO 25
<211> LENGTH: 45
<212> TYPE: PRT
<213> ORGANISM: Homo sapiens

<400> SEQUENCE: 25

```
Cys Phe Asp His Ala Ala Gly Thr Ser Tyr Val Val Gly Glu Thr Trp
1               5                   10                  15
Glu Lys Pro Tyr Gln Gly Trp Met Met Val Asp Cys Thr Cys Leu Gly
            20                  25                  30
Glu Gly Ser Gly Arg Ile Thr Gly Thr Ser Arg Asn Arg
        35                  40                  45
```

<210> SEQ ID NO 26
<211> LENGTH: 42
<212> TYPE: PRT
<213> ORGANISM: Homo sapiens

<400> SEQUENCE: 26

```
Cys Asn Asp Gln Asp Thr Arg Thr Ser Tyr Arg Ile Gly Asp Thr Trp
1               5                   10                  15
Ser Lys Lys Asp Asn Arg Gly Asn Leu Leu Gln Cys Ile Cys Thr Gly
            20                  25                  30
Asn Gly Arg Gly Glu Trp Lys Cys Glu Arg
        35                  40
```

<210> SEQ ID NO 27
<211> LENGTH: 35
<212> TYPE: PRT
<213> ORGANISM: Homo sapiens

<400> SEQUENCE: 27

His Thr Ser Val Gln Thr Thr Ser Ser Gly Ser Gly Pro Phe Thr Asp
1               5                   10                  15

Val Arg Ala Ala Val Tyr Gln Pro Gln Pro His Pro Gln Pro Pro Pro
                20                  25                  30

Tyr Gly His
        35

<210> SEQ ID NO 28
<211> LENGTH: 37
<212> TYPE: PRT
<213> ORGANISM: Homo sapiens

<400> SEQUENCE: 28

Cys Val Thr Asp Ser Gly Val Val Tyr Ser Val Gly Met Gln Trp Leu
1               5                   10                  15

Lys Thr Gln Gly Asn Lys Gln Met Leu Cys Thr Cys Leu Gly Asn Gly
                20                  25                  30

Val Ser Cys Gln Glu
            35

<210> SEQ ID NO 29
<211> LENGTH: 45
<212> TYPE: PRT
<213> ORGANISM: Homo sapiens

<400> SEQUENCE: 29

Thr Ala Val Thr Gln Thr Tyr Gly Gly Asn Ser Asn Gly Glu Pro Cys
1               5                   10                  15

Val Leu Pro Phe Thr Tyr Asn Asp Arg Thr Asp Ser Thr Thr Ser Asn
                20                  25                  30

Tyr Glu Gln Asp Gln Lys Tyr Ser Phe Cys Thr Asp His
            35                  40                  45

<210> SEQ ID NO 30
<211> LENGTH: 65
<212> TYPE: PRT
<213> ORGANISM: Homo sapiens

<400> SEQUENCE: 30

Thr Val Leu Val Gln Thr Arg Gly Gly Asn Ser Asn Gly Ala Leu Cys
1               5                   10                  15

His Phe Pro Phe Leu Tyr Asn Asn His Asn Tyr Thr Asp Cys Thr Ser
                20                  25                  30

Glu Gly Arg Arg Asp Asn Met Lys Trp Cys Gly Thr Thr Gln Asn Tyr
            35                  40                  45

Asp Ala Asp Gln Lys Phe Gly Phe Cys Pro Met Ala Ala His Glu Glu
        50                  55                  60

Ile
65

<210> SEQ ID NO 31
<211> LENGTH: 48
<212> TYPE: PRT
<213> ORGANISM: Homo sapiens

<400> SEQUENCE: 31

Cys Thr Thr Asn Glu Gly Val Met Tyr Arg Ile Gly Asp Gln Trp Asp
1               5                   10                  15

Lys Gln His Asp Met Gly His Met Met Arg Cys Thr Cys Val Gly Asn
                20                  25                  30

```
Gly Arg Gly Glu Trp Thr Cys Ile Ala Tyr Ser Gln Leu Arg Asp Gln
        35                  40                  45

<210> SEQ ID NO 32
<211> LENGTH: 43
<212> TYPE: PRT
<213> ORGANISM: Homo sapiens

<400> SEQUENCE: 32

Cys Ile Val Asp Asp Ile Thr Tyr Asn Val Asn Asp Thr Phe His Lys
 1               5                  10                  15

Arg His Glu Glu Gly His Met Leu Asn Cys Thr Cys Phe Gly Gln Gly
            20                  25                  30

Arg Gly Arg Trp Lys Cys Asp Pro Val Asp Gln
        35                  40

<210> SEQ ID NO 33
<211> LENGTH: 48
<212> TYPE: PRT
<213> ORGANISM: Homo sapiens

<400> SEQUENCE: 33

Cys Gln Asp Ser Glu Thr Gly Thr Phe Tyr Gln Ile Gly Asp Ser Trp
 1               5                  10                  15

Glu Lys Tyr Val His Gly Val Arg Tyr Gln Cys Tyr Cys Tyr Gly Arg
            20                  25                  30

Gly Ile Gly Glu Trp His Cys Gln Pro Leu Gln Thr Tyr Pro Ser Ser
        35                  40                  45

<210> SEQ ID NO 34
<211> LENGTH: 39
<212> TYPE: PRT
<213> ORGANISM: Homo sapiens

<400> SEQUENCE: 34

Ser Gly Pro Val Glu Val Phe Ile Thr Glu Thr Pro Ser Gln Pro Asn
 1               5                  10                  15

Ser His Pro Ile Gln Trp Asn Ala Pro Gln Pro Ser His Ile Ser Lys
            20                  25                  30

Tyr Ile Leu Arg Trp Arg Pro
        35

<210> SEQ ID NO 35
<211> LENGTH: 10
<212> TYPE: PRT
<213> ORGANISM: Homo sapiens

<400> SEQUENCE: 35

Val Ser Ile Pro Pro Arg Asn Leu Gly Tyr
 1               5                  10

<210> SEQ ID NO 36
<211> LENGTH: 2
<212> TYPE: PRT
<213> ORGANISM: Homo sapiens

<400> SEQUENCE: 36

Val Ser
 1

<210> SEQ ID NO 37
```

```
<211> LENGTH: 4
<212> TYPE: PRT
<213> ORGANISM: Homo sapiens

<400> SEQUENCE: 37

Ser Tyr Gln Phe
 1

<210> SEQ ID NO 38
<211> LENGTH: 33
<212> TYPE: PRT
<213> ORGANISM: Homo sapiens

<400> SEQUENCE: 38

Trp Phe Leu Phe Phe Pro Ala Phe Glu Pro Thr Thr Leu Ile Asn Tyr
 1               5                  10                  15

Ser Tyr Ser Ile Tyr Tyr Ile Cys Leu Val Asn Lys Gln Tyr Val Val
                20                  25                  30

Asn

<210> SEQ ID NO 39
<211> LENGTH: 3
<212> TYPE: PRT
<213> ORGANISM: Homo sapiens

<400> SEQUENCE: 39

Ile Asp Leu
 1

<210> SEQ ID NO 40
<211> LENGTH: 8
<212> TYPE: PRT
<213> ORGANISM: Homo sapiens

<400> SEQUENCE: 40

Thr Glu Lys Lys Lys Lys Lys Lys
 1               5

<210> SEQ ID NO 41
<211> LENGTH: 10
<212> TYPE: PRT
<213> ORGANISM: Homo sapiens

<400> SEQUENCE: 41

Val Ser Ile Pro Pro Arg Asn Leu Gly Tyr
 1               5                  10
```